(12) United States Patent
Dalton et al.

(10) Patent No.: US 7,622,503 B2
(45) Date of Patent: Nov. 24, 2009

(54) SELECTIVE ANDROGEN RECEPTOR MODULATORS AND METHODS OF USE THEREOF

(75) Inventors: James T. Dalton, Upper Arlington, OH (US); Duane D. Miller, Germantown, TN (US); Karen A. Veverka, Cordova, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 11/146,427

(22) Filed: Jun. 7, 2005

(65) Prior Publication Data

US 2006/0035965 A1    Feb. 16, 2006

Related U.S. Application Data

(63) Continuation-in-part of application No. 10/961,380, filed on Oct. 12, 2004, application No. 11/146,427, which is a continuation-in-part of application No. 10/861,923, filed on Jun. 7, 2004, which is a continuation-in-part of application No. 10/310,150, filed on Dec. 5, 2002, application No. 11/146,427, which is a continuation-in-part of application No. 10/863,524, filed on Jun. 9, 2004, now abandoned, which is a continuation-in-part of application No. 10/371,213, filed on Feb. 24, 2003, now Pat. No. 7,026,500, which is a continuation-in-part of application No. 10/270,232, filed on Oct. 15, 2002, now Pat. No. 6,838,484, which is a continuation-in-part of application No. 09/935,045, filed on Aug. 23, 2001, now Pat. No. 6,569,896.

(60) Provisional application No. 60/510,138, filed on Oct. 14, 2003, provisional application No. 60/336,185, filed on Dec. 6, 2001, provisional application No. 60/300,083, filed on Jun. 25, 2001, provisional application No. 60/367,355, filed on Aug. 24, 2000.

(51) Int. Cl.
  *A61K 31/275* (2006.01)
  *A61K 31/165* (2006.01)
(52) U.S. Cl. .................. 514/522; 514/524; 514/619
(58) Field of Classification Search ............... 514/522, 514/524, 619
See application file for complete search history.

(56) References Cited

U.S. PATENT DOCUMENTS

| | | | |
|---|---|---|---|
| 3,239,345 A | 3/1966 | Hodge et al. | |
| 3,865,801 A | 2/1975 | Chiba et al. | |
| 3,875,229 A | 4/1975 | Gold | |
| 4,036,979 A | 7/1977 | Asato | |
| 4,139,638 A | 2/1979 | Neri et al. | |
| 4,191,775 A | 3/1980 | Glen | |
| 4,239,776 A | 12/1980 | Glen et al. | |
| 4,282,218 A | 8/1981 | Glen et al. | |
| 4,386,080 A | 5/1983 | Crossley et al. | |
| 4,411,890 A | 10/1983 | Momany et al. | |
| 4,465,507 A | 8/1984 | Konno et al. | |
| 4,636,505 A * | 1/1987 | Tucker | 514/256 |
| 4,880,839 A | 11/1989 | Tucker | |
| 4,977,288 A | 12/1990 | Kassis et al. | |
| 5,162,504 A | 11/1992 | Horoszewicz | |
| 5,179,080 A | 1/1993 | Rothkopf et al. | |
| 5,441,868 A | 8/1995 | Lin et al. | |
| 5,547,933 A | 8/1996 | Lin et al. | |
| 5,609,849 A | 3/1997 | Kung | |
| 5,612,359 A | 3/1997 | Murugesan et al. | |
| 5,618,698 A | 4/1997 | Lin et al. | |
| 5,621,080 A | 4/1997 | Lin et al. | |
| 5,656,651 A | 8/1997 | Sovak et al. | |
| 6,019,957 A | 2/2000 | Miller et al. | |
| 6,043,265 A | 3/2000 | Murugesan et al. | |
| 6,071,957 A | 6/2000 | Miller et al. | |
| 6,160,011 A * | 12/2000 | Miller et al. | 514/522 |
| 6,482,861 B2 | 11/2002 | Miller et al. | |
| 6,492,554 B2 | 12/2002 | Dalton et al. | |
| 6,548,529 B1 | 4/2003 | Robl et al. | |
| 6,569,896 B2 | 5/2003 | Dalton et al. | |
| 6,777,427 B2 | 8/2004 | Miyakawa et al. | |
| 6,838,484 B2 * | 1/2005 | Steiner et al. | 514/616 |
| 6,899,888 B2 * | 5/2005 | Steiner et al. | 424/423 |
| 6,960,474 B2 | 11/2005 | Salvati et al. | |
| 6,995,284 B2 * | 2/2006 | Dalton et al. | 564/155 |
| 6,998,500 B2 | 2/2006 | Dalton et al. | |
| 7,026,500 B2 | 4/2006 | Dalton et al. | |

(Continued)

FOREIGN PATENT DOCUMENTS

AU    2002364949    6/2003

(Continued)

OTHER PUBLICATIONS

U.S. Appl. No. 09/935,044, filed Aug. 23, 2001, Dalton et al.

(Continued)

*Primary Examiner*—Shailendra Kumar
(74) *Attorney, Agent, or Firm*—Pearl Cohen Zedek Latzer, LLP; Mark S. Cohen

(57) ABSTRACT

This invention provides SARM compounds and their use in treating a variety of diseases or conditions in a subject, including, inter-alia, a muscle wasting disease and/or disorder or a bone-related disease and/or disorder.

23 Claims, 15 Drawing Sheets

U.S. PATENT DOCUMENTS

| | | | |
|---|---|---|---|
| 7,041,844 | B2 | 5/2006 | Miller et al. |
| 7,344,700 | B2 | 3/2008 | Dalton et al. |
| 2001/0012839 | A1 | 8/2001 | Miller et al. |
| 2002/0173445 | A1 | 11/2002 | Salvati et al. |
| 2003/0232792 | A1 | 12/2003 | Dalton et al. |
| 2004/0014975 | A1 | 1/2004 | Dalton et al. |
| 2004/0029913 | A1 | 2/2004 | Dalton et al. |
| 2004/0053897 | A1 | 3/2004 | Steiner et al. |
| 2004/0087557 | A1 | 5/2004 | Steiner et al. |
| 2004/0087810 | A1 | 5/2004 | Dalton et al. |
| 2004/0147489 | A1 | 7/2004 | Dalton et al. |
| 2004/0260092 | A1 | 12/2004 | Miller et al. |
| 2005/0137172 | A1 | 6/2005 | Dalton et al. |
| 2006/0183931 | A1 | 8/2006 | Dalton et al. |
| 2007/0066568 | A1 | 3/2007 | Dalton et al. |
| 2007/0123563 | A1 | 5/2007 | Dalton et al. |
| 2007/0173546 | A1 | 7/2007 | Dalton et al. |

FOREIGN PATENT DOCUMENTS

| | | |
|---|---|---|
| AU | 2003216174 | 9/2003 |
| CA | 2420279 | 2/2002 |
| CA | 2477737 | 9/2003 |
| CA | 2502209 | 4/2004 |
| CA | 2502355 | 4/2004 |
| CA | 2538095 | 4/2004 |
| CA | 25029464 | 6/2005 |
| EP | 0 040 932 | 2/1981 |
| EP | 0 100 172 | 2/1984 |
| EP | 00 02 892 | 2/1985 |
| EP | 000 2892 | 2/1985 |
| EP | 0253 503 | 12/1991 |
| EP | 0253503 | 12/1991 |
| EP | 668351 | 8/1995 |
| EP | 1221439 | 7/2002 |
| EP | 1401801 | 11/2006 |
| EP | 1801140 | 6/2007 |
| GB | 1360001 | 3/1970 |
| JP | 52-128329 | 10/1977 |
| JP | 54-63047 | 12/1980 |
| JP | 59-033250 | 2/1984 |
| WO | WO 98/07110 | 8/1989 |
| WO | WO 98/07111 | 8/1989 |
| WO | WO 91/05867 | 5/1991 |
| WO | WO 93/04081 | 3/1993 |
| WO | WO 95/19770 | 7/1995 |
| WO | WO 98/05962 | 2/1998 |
| WO | WO 98 05962 | 2/1998 |
| WO | WO 98/53826 | 12/1998 |
| WO | WO 98/55153 | 12/1998 |
| WO | WO 00/01389 | 1/2000 |
| WO | WO/01/27086 | 4/2001 |
| WO | WO 01/27086 | 4/2001 |
| WO | WO 01 27622 | 4/2001 |
| WO | WO 01/27622 | 4/2001 |
| WO | WO 01/28990 | 4/2001 |
| WO | WO 01 28990 | 4/2001 |
| WO | WO 01/34563 | 5/2001 |
| WO | WO 01 34563 | 5/2001 |
| WO | WO 01/68603 | 9/2001 |
| WO | WO 02 00617 | 1/2002 |
| WO | WO 02/00617 | 2/2002 |
| WO | WO 02/016310 | 2/2002 |
| WO | WO 02/16310 | 2/2002 |
| WO | WO/02/22585 | 3/2002 |
| WO | WO 02/22585 | 3/2002 |
| WO | WO 03/011302 | 2/2003 |
| WO | WO 03/049675 | 6/2003 |
| WO | WO 03/065992 | 8/2003 |
| WO | WO 03/074449 | 9/2003 |
| WO | WO 03/077919 | 9/2003 |
| WO | WO/03/077919 | 9/2003 |
| WO | WO 2004/035736 | 4/2004 |
| WO | WO 2005/000794 | 1/2005 |
| WO | WO 2005/060647 | 7/2005 |

OTHER PUBLICATIONS

U.S. Appl. No. 09/935,045, filed Aug. 23, 2001, Dalton et al.
U.S. Appl. No. 09/644,970, filed Aug. 2, 2000, Dalton et al.
Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.
Berger et al., "Concepts and limitations in the application of radiolabeled antiandrogens, estrogens, or androgens as isotropic scanning agents for the prostate", Invest. Urol, (1975), 1391, 10-16.
Howard Tucker and Glynne J. Chesterson, J. Med Chem. 1988, 31, pp. 885-887, "Resolution of the Nonsteroidal Antiandrogen -4'-Cyano-3-[(4-fluorophenyl)sulfonyl]-2-hydroxy-2-methyl-3'-(trifluoromethyl)-propionanilide and the Determination of the Absolute Configuration of the Active Enantiomer".
D. McKillop, et al, "Enantioselective metabolism and pharmacokinetics of Casodex in the male rat", Xenobiotica, 1995, vol. 25, No. 6, 623-634.
Leonid Kirkovsky, et al., "[$^{125}$I]-Radionated Bicalutamide Analogs as Potential Imaging Agents for Prostate Cancer", Poster Presentation MEDI 155, 214th ACS National Meeting, Las Vegas, NV, Sep. 7-11, 1997, Deparment of Pharmaceutical Sciences, University of Tennessee, Memphis, TN 38163.
David T. Baird and Anna F. Glasier, "Hormonal Contraception—Drug Therapy", the New England Journal of Medicine, May 27, 1993, pp. 1543-1549.
F.C. W. Wu, "Male Contraception: Current Status and Future Prospects", Clinical Endocrinology, (1988), 29, pp. 443-465.
Carl Djerassi and S.P. Leibo, "A new look at male contraception", Nature, vol. 370, pp. 11-12.
World Health Organisation Task Force on Methods for the Regulation of Male Fertility, "Contraceptive efficacy of testosterone-induced azoospermia in normal men", the Lancet, vol. 336, Oct. 20, 1990, pp. 955-959 and 1517-1518.
C. G. Francisco, et al., "Long-acting contraceptive agents: testosterone esters of unsaturated acids", Steroids, Jan. 1990, vol. 55, Butterworths.
John M. Hoberman and Charles E. Yesalis, "The History of Synthetic Testosterone", Scientific American, Feb. 1995, pp. 76-81.
Leonid Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.
Edwards JP, Higuchi RI, Winn DT, Pooley CLF, Caferro TR, Hamann LG, Zhi L. Marschke KB, Goldman ME, and Jones TK. Nonsteroidal androgen receptor agonists based on 4-(trifluoromethyl)-2H-pyrano[3,2-g]quinolin:2-one. Bioorg. Med. Chem. Lett., 9:1003, 1999.
Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009. 1999.
Higuchi RI, Edwards JP, Caferro TR, Ringgeriberg JD, Kong JW, Hamann LG, Arienti KL, Marschke KB, Davis RL, Farmer LJ, and Jones TK. 4-Alkyl- and 3,4-diaklyl-l,2,3,4-tetrahydro-8-pyridono[5,6-g]quinolines: potent, nonsteroidal androgen receptor agonists. Bioorg. Med. Chem. Lett., 9:1335,1999.
Hamann LG, Mani NS, Davis RL, Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210, 1999.
Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38: 4855, 1995.

Dalton JT, Mukherjee A, Zhu Z, Kirkovsky L, and Miller DD. Discovery of Nonsteroidal Androgens. Biochem. Biophys. Res. Commun.,244(1):1-4, 1998.

Edwards JP, West SJ, Pooley CLF, Marschke KB, Farmer IJ, and Jones TK. New nonsteroidal androgen receptor modulators based on 4-(trifluoromethyl)-2-(1H)-Pyrololidino[3,2-g]quinolone. Bioorg. Med. Chem. Lett., 8: 745, 1998.

Buchwald, et Long-term, continuous intravenous heparin administration by an implantable infusion pump in ambulatory patients with recurrent venous thrombosis.Surgery. 1980 88(4)507-16.

Wahner, et al (1984) "Assesment of Bone Mineral Part 1 " J Nucl. Medicine 1134-1141.

Wahner, et al (1985) "Bone Mineral Density of the Radius" J. Nucl Medicine 26 13-39.

Faulkner KG, et al (1991) "Noninvasive measurements of bone mass, structure, and strength: current methods and experimental techniques." Am J Rosentgenology 157:1229-1237.

Hanada, K., et al (2003) "Bone anabolic effects of S-40503, a novel nonsteroidal selective androgen receptor modulator (SARM), in rat models of osteoporosis." Biol. Pharm. Bull. 26:1563-1569.

Kalu, DN, (1991) "The ovariectomized rat model of postmenopausal bone loss. Bone Miner." 15 175-91.

Negro-Vilar, A. (1999) "Selective androgen receptor modulators (SARMs): a novel approach to androgen therapy for the new illennium." J. Clin. Endocrin Metabol. 84: 3459-3462.

Campfield et al., 1995, "Recombinant mouse OB protein: evidence for a peripheral signal linking adiposity and central neural networks" *Science* 269:546-549.

Considine et al., 1995, "Evidence against either a premature stop codon or the absence of obese gene mRNA in human obesity." J. Clin. Invest. 95:2986-2988.

Grundy, 1990, *Disease-a-Month* 36:645-696.

Halaas et al., 1995, "Weight-reducing effects of the plasma protein encoded by the obese gene." *Science* 269:543-546.

Hamilton et al., 1995, a Increased obese mRNA expression in omental fat cells from massively obese humans. Nature Med. 1:953.

Lonnquist et al., 1995, Nature Med. 1:950.

Matsumoto, 1994, "Hormonal therapy of male hypogonadism" Endocrinol. Met. Clin. N. Am. 23:857-75.

Pelleyrnounter et al, 1995, "Effects of the obese gene product on body weight regulation in ob/ob mice." *Science* 269:540-543.

Singh et al., 2003, "Androgens stimulate myogenic differentiation and inhibit adipogenesis in C3H 10T1/2 pluripotent cells through an androgen receptor-mediated pathway." *Endocrinology*, 144(1 I):5081-8.

Sefton, 1987, "Implantable pumps." CRC Crit. Ref. Biomed. Eng. 14:201.

U.S. Appl. No. 09/644,970, filed Aug. 2, 2000, Dalton et al.

Matsumoto, "Hormonal terapy of male hypogonadism" Endocrinol. Met. Clin. N. Am.: 23:857-75 (1994).

Zhou et al., Molec. Endocrinol. 9: 208-18 (1995).

Sundaram et al., "7 Alpha-Methyl-Nortestosterone (MENT): The Optimal Androgen for Male Contraception", Ann. Med., 25:199-205 (1993).

Wahner H W et al., "Assesment of Bone Mineral Part 1", J Nucl Medicine, pp. 1134-1141 (1984).

Wahner H W et al., "Bone Mineral Density of the Radius", J Nucl Medicine, 26:13-39 (1985).

Singh et al., "Androgens stimulate myogenic differentiation and inhibit adipogenesis in C3H 10T1/2 pluripotent cells through an androgen receptor-mediated pathway" Endocrinology,144(11):5081-8, Jul. 24, 2003.

Langer, "New methods of drug delivery", Science 249:1527-1533(1990).

Treat et al., in Liposomes in the Therapy of infections disease and cancer, Lopez-Berestein and Fidler (eds.), Liss New York, pp. 353-365 (1989).

Sefton, "Implantable pumps" CRC Crit. Ref. Biomed. Eng. 14:201 (1987).

Campfield et al., 1995, "Recombinant mouse OB protein: evidence for a peripheral signal linking adiposity and central neural networks" Science 269:546-549.

Dalton et al., "Therapeutic Promise of Selective Androgen Receptor Modulators (SARSs): Preclinical and Clinical Proof-of-Concept Studies" —The Endocrine Society—Programs and Abstracts—89th Annual Meeting- Paper S41-2.

Goodson, in Medical Applications of controlled Release, supra, vol. 2, pp. 115-138 (1984).

Narayanan et al., "Steroidal Androgens and Nonsteroidal, Tissue Selective Androgen Receptor Modulators (SARM) Regulate Androgen Receptor Function Through Distinct Genomic and Non-Genomic Signaling Pathways" The Endocrine Society—Programs and Abstracts—89th Annual Meeting—Paper P1-595.

Edwards, J. P. et al., Bio. Med. Chem. Let., 9,1003-1008(1999).

Pelleymounter et al., 1995, "Effects of the Obese gene product on body weight regulation in ob/ob mice", Science 269:540-543.

Steinberger et al., Effect of chronic Administration of Testosterone Enanthateon Sperm Production and Plasma Testosterone, Follicle Stimulating Hormone, and Luteinizing Hormone Levels: a Preliminary Evaluation of possible Male Contraceptive, Fertility and Sterility 28:1320-28 (1977).

World Health Organization Task Force on Methods and Regulation of Male Fertility "Contraceptive Efficacy of Testosterone-Induced Azoospermia and Oligospermia in Normal Men", Fertility & Sterility 65:821-29 (1996).

Wu, "Effects of Testosterone Enanthate in Normal Men: Experience from a Multicenter contraceptive efficacy study", Fertility and Sterility 65:626-36 (1996).

International Search Report of Application No. PCT/US08/04816 issued on Jul. 08, 2008.

International Search Report of Application No. PCT/US05/19788 issued on Jun. 16, 2006.

Georgian Search Report of Application No. AP 2005 009805 issued on Jan. 23, 2008.

Supplementary European Search Report of Application No. EP 05 75 8756 issued on May 29, 2008.

Kalu, DN (1991) "The ovariectomized rat model of postmenopausal bone loss Bone Miner" 15:175-91.

Considine et al., 1995, "Evidence against either a premature stop codon or the absence of obese gene Mrna in human obesity", J. Clin. Invest. 95:2986-2988.

Tucker et al "Nonsteroidal antiandrogens. Synthesis and structure-activity relationships of 3-substituted derivatives of 2-hydroxypropionanilides." *J. Med Chem* (1988), 31, 954-959.

Buchwald et al. "Long-term, continuous intravenous heparin administration by an implantable infusion pump in ambulatory patients with recurrent venous thrombosis."Surgery 88:507 (1980).

Saudek et al."A preliminary trial of the programmable implantable medication system for insulin delivery." N. Engl. J. Med. 321:574 (1989).

Corey (1987) "Asymmetric Bromolactonization Reaction: Synthesis of Optically Active 2-hydroxy-2-Methylalkanoic Acids from 2-Methylalkanoic Acids" Tetrahedron Letters vol. 28, No. 25 2801-2804.

Kirkovsky et al., "Approaches to Irreversible non-steroidal chiral antiandrogen", Department of Pharmaceutical Sciences, University of Tennessee, 47th Southeast/51st Southeast Joint Regional Meeting of the American Chemical Society, Memphis, TN, Nov. 29-Dec. 1, 1995.

Eliason et al., "High Throughput Fluorescence Polarization-Based Screening Assays for the Identification of Novel Nuclear Receptor Ligands", Abstracts of Papers, 223rd ACS National Meeting, Orlando, FL, United States, (2002), Apr. 7, 2002.

Berger et al., "Concepts and Limitations in the application of radiolabeled antiandrogens, estrogens, or androgen as isotropic scanning agents for the prostate", Invest. Urol, (1975), 1391, 10-16.

Tucker and Chesterson, J. Med Chem. 1988, 31, pp. 885-887, "Resolution of the Nonsteroidal Antiandrogen- 4'-Cyano-3-[(4-fluorophenyl)sulfonyl]-2-hydroxy-2-methyl-3'-(trifluoromethyl)-propionanilide and the Determination of the Absolute Configuration of the Active Enantiomer".

D. McKillop, et al., "Enantioselective metabolism and pharmacokinetics of Casodex in the male rat", Xenobiotica, 1995, vol. 25, No. 6, 623-634.

Leonid Kirkovsky, et al., "[$^{125}$I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.

David T. Baird and Anna F. Glasier, "Hormonal Contraception—Drug Therapy", the New England Journal of Medicine, May 27, 1993, pp. 1543-1549.

Wu, "Male Contraception: Current Status and Future Prospects", Clinical Endocrinology, (1988), 29, pp. 443-465.

Carl Djerassi and S.P. Leibo, "A new look at male contraception", Nature, vol. 370, pp. 11-12.

World Health Organisation Task Force on Methods for the Regulation of Male Fertility, "Contraceptive efficacy of testosterone-induced azoospermia in normal men", the Lancet, vol. 336, Oct. 20, 1990, pp. 955-959 and 1517-1518.

C. G. Francisco, et al., "Long-acting contraceptive agents: testosterone esters of unsaturated acids", Steroids, Jan. 1990, vol. 55, Butterworths.

John M. Hoberman and Charles E. Yesalis, "The History of Synthetic Testosterone", Scientific American, Feb. 1995, pp. 76-81.

David J. Handelsman, "Bridging the gender gap in contraception: another hurdle cleared" The Medical Journal of Australia, vol. 154, Feb. 18, 1996, pp. 230-233.

Edwards JP, Higuchi RI, Winn DT, Pooley CLF Caferro TR, Hamann LG, Zhi L, Marschke KB, Goldman ME, and Jones TK. Nonsteroidal androgen receptor agonists based on 4-(trifluoromethyl)-2H-pyrano [3, 2-g] quinolin-2-one. Bioorg. Med. Chem. Lett., 9: 1003, 1999.

Mukherjee A, Kirkovsky L, Yao XT, Yates CR, and Dalton JT. Enantioselective Binding of Casodex to the Androgen Receptor. Xenobiotica 26(2): 117-122, 1996.

Dalton JT, Mukherjee A, Zhu Z, Kirkovsky L; and Miller DD. Discovery of Nonsteroidal Androgens. Biochemical and Biophysical Research Communications, 244(1): 1-4, 1998.

Mukherjee A, Kirkovsky LI, Kimura Y, Marvel MM, Miller DD, and Dalton JT. Affinity Labeling of the Androgen Receptor with Nonsteroidal Chemoaffinity Ligands. Biochemical Pharmacology, 58: 1259-1267, 1999.

Kirkovsky L, Mukherjee A, Yin D, Dalton JT, and Miller DD. Chiral Nonsteroidal Affinity Ligands for the Androgen Receptor. 1. Bicalutamide Analogs bearing Electrophilic Groups at the Aromatic Ring B. Journal of Medicinal Chemistry, 43: 581-590, 2000.

Marhefka CA, Moore Iibm, Bishop TC, Kirkovsky L, Mukherjee A, Dalton JT, Miller DD. Homology Modeling Using Multiple Molecular Dynamics Simulations and Docking Studies of the Human Androgen Receptor Ligand Binding Domain Bound to Testosterone and Nonsteroidal Ligands. Journal of Medicinal Chemistry, 44: 1729-1740, 2001.

He Y, Yin D, Perera MA, Kirkovsky L, Stourman N, Dalton JT, and Miller DD. Novel Nonsteroidal Ligands with High Affinity and Potent Functional Activity for the Human Androgen Receptor. European Journal of Medicinal Chemistry, 37: 619-634, 2002.

Yin D, He Ys Hong SS, Marhefka CA, Stourman N, Kirkovsky L, Miller DD, and Dalton JT. Key Structural Features of Nonsteroidal Ligands for Binding and Activation of the Androgen Receptor. Molecular Pharmacology, 63:211-223, 2003.

Yin D, Xu H, He Y, Kirkovsky L, Miller DD, and Dalton JT, Pharmacology, Pharmacokinetics and Metabolism of Acetothiolutamide, A Novel Nonsteroidal Agonist For the Androgen Receptor. Journal of Pharmacology and Experimental Therapeutics, 304(3):1323-1333, 2003.

Yin D, Gao W, Kearbey JD, Xu H, Chung K, Miller DD, and Dalton JT. Pharmacodynamics of Selective Androgen Receptor Modulators. Journal of Pharmacology and Experimental Therapeutics, 304(3): 1334-1340, 2003.

Wu Z, Gao W, Phelps M, Wu D, Miller DD, and Dalton JT. The Favorable Effects of Weak Acids on Negative-Ion Electrospray Mass Spectrometry. Analytical Chemistry, 76(3):839-847, 2004.

Kearbey, J. D., Wu, D., Gao, W., Miller, D. D., and Dalton, J. T. (2004). Pharmacokinetics of S-3-(4-acetylamino-phenoxy)-2-hydroxy-2-methyl-N-(4-nitro- 3-trifluoromethyl-phenyl)-propionamide in rats, a non-steroidal selective androgen receptor modulator. Xenobiotica 34(3), 273-80.

Marhefka, C. A., Gao, W., Chung, K., Kim, J., He, Y., Yin, D., Bohl, C., Dalton, J. T., and Miller, D. D. (2004). Design, synthesis, and biological characterization of metabolically stable selective androgen receptor modulators. J Med Chem 47(4), 993-8.

Bahl CE, Chang C, Mohler ML, Miller DD, Swaan PW, and Dalton JT. A Ligand-Based Approach to Identify Quantitative Structure-Activity Relationships for the Androgen Receptor. Journal of Medicinal Chemistry, 47(15):3765-3776, 2004.

Gao, W., Kearbey, J.D., Nair, V.A, Chung, K., Partow, A.F., Miller, D.D., and Dalton, J.T. Comparison of the Pharmacological Effects of a Novel Selective Androgen Receptor Modulator (SARM), the 5{alpha}-Reductase Inhibitor Finasteride, and the Antiandrogeo Hydroxyflutamide in Intact Rats: New Approach for Benign Prostate Hyperplasia (BPH). Endocrinology, 145(12): 5420-5428, 2004.

Nair VA, Mustafa SM$_3$ Mohler ML, Fisher SJ, Dalton JT, and Miller DD. Synthesis of Novel Iodo Derived Bicalutamide Analogs. Tetrahedron Letters, 45: 9475-9477, 2004.

Chen J, Hwang DJ, Bohl CE, Miller DD, and Dalton JT. A Selective Androgen Receptor Modulator (SARM) for Hormonal Male Contraception. Journal of Pharmacology and Experimental Therapeutics, 312(2): 546-553,2005.

Nair V, Mustafa SM, Mohler ML, Fisher S J, Dalton JT, and Miller DD. Synthesis of irreversibly binding bicalutamide analogs for imaging studies. Tetrahedron Letters. 46:4821-4823, 2005.

Bohl CE, Gao W, Miller DD, Bell CE, Dalton JT. Structural Basis for Antagonism and Resistance of Bicalutamide in Prostate Cancer. Proc Natl Acad Sci USA. 102(17): 6201-6206, 2005.

Chen J, Kim J, and Dalton JT. Discovery and Therapeutic Promise of Selective Androgen Receptor Modulators. Molecular Interventions, 5(3):173-188, 2005.

Kim J, Wu D, Hwang DJ, Miller DD, and Dalton JT. The 4-Para-Substituent of S-3-(Phenoxy)-2-hydroxy-2-methyl-N-(4-nitro-3-trifluoromethyl-phenyl)-propionamides is a Major Structural Determinant of in Vivo Disposition and Activity of Selective Androgen Receptor Modulators. Journal of Pharmacology and Experimental Therapeutics, 315(I):230-239, 2005.

Gao W, Reiser PJ, Coss CC, Phelps MA, Kearbey JD, Miller DD, and Dalton JT. Selective Androgen Receptor Modulator (SARM) Treatment Improves Muscle Strength and Body Composition, and Prevents Bone Loss in Orchidectomized Rats. Endocrinology, 146(11):48B7-4897, 2005.

Bohl CE, Miller DD, Chen J, Bell CE, and Dalton JT. Structural Basis for Accomodation of Nonsteroidal Ligaiids in the Androgen Receptor. Journal of Biological Chemistry, 280(45):37747-37754, 2005.

Gao W, Bohl CE, and Dalton JT. Chemistry and structural biology of androgen receptor. Chemical Reviews, 1G5(9):3352-70,2005.

Chen J, Hwang DJ, Chung K, Bohl CE, Fisher SJ, Miller DD, Dalton JT. In vitro and in vivo structure-activity relationships of novel androgen receptor ligands with multiple substituents in the B-ring. Endocrinology, 146(12):5444-54, 2005.

Segal S, Narayanan R, Dalton JT. Therapeutic potential of the SARMs: revisiting the androgen receptor for drug discovery. Expert Opinion in Investigational Drugs. 15(4):377-87, 2006.

Gao W, Johnston JS, Miller DD, Dalton JT. Inter-Species Differences in Pharmacokinetics and Metabolism of S-3-(4-acelylamino-phenoxy)-2-hydroxy-2-methyl-N-(4-nitro- 3-trifluoromethyi-phenyl>propionamide: The Role of N-Acetyltransferase. Drug Metabolism and Disposition, 34(2):254-260, 2006.

Gao W, Wu Z, Bohl CE, Yang J, Miller DD, Dalton JT. Characterization of the In vitro Metabolism of Selective Androgen Receptor Modulator (SARM) Using Human, Rat and Dog Liver Enzyme Preparations. Drug Metabolism and Disposition, 34(2):243-253, 2006.

Wu D, Wu Z, Yang J, Nair VA, Miller DD, Dalton JT. Pharmacokinetics and metabolism of a selective androgen receptor modulator (SARM) in rats-implication of molecular properties and intensive metabolic profile to investigate ideal pharmacokinetic characteristics of a propanamide in preclinical study. Drug Metabolism and Disposition, 34(3):483-494, 2006.

Yang J, Bohl CE, Nair VA, Mustafa SM, Hong SS, Miller DD, Dalton JT. Preclinical pharmacology of a nonsteroidal ligand for androgen receptor mediated imaging of prostate cancer. Journal of Pharmacology and Experimental Therapeutics, 317(I):402-408, 2006.

Gao W, Kim J, Dalton JT, Pharmacokinetics and Pharmacodynamics of Nonsteroidal Androgen Receptor Ligands. Pharmaceutical Research, 23(8):1641-165B, 2006.

Hwang DJ, Yang J, Xu H, Rakov IM, Mohler ML, Dalton JT, Miller DD-Aryl isothiocyanato selective androgen receptor modulators (SARMs) for prostate cancer. Bioorganic and Medicinal Chemistry, ,14(19):6525-6538, 2006.

Bhasin S, Calof OM, Storer TW, Lee ML, Mazer NA, Jasuja R, Montori VM, Gao W, Dalton JT. Drug insight: Testosterone and selective androgen receptor modulators as anabolic therapies for chronic illness and aging. Nature, Clinical Practice in Endocrinology and Metabolism, 2(3): 146-159,2006.

Nair VA; Mustafa SM; Mohler ML; Dalton JT; Miller DD.Synthesis of oxazolidinedione derived bicalutamide analogs. Tetrahedron Letters, 47 (23): 3953-3955, 2006-.

Patil R, Li W, Ross CR, Kraka E, Cremer D, Mohler ML, Dalton JT, and Miller DD. Cesium fluoride and tetra-n-butylammonium fluoride mediated 1,4-N-O shiftof disubstituted phenyl ring of a bicalutamide derivative. Tetrahedron Letters, 47:3941-3944, 2006.

Kearbey JD, Gao W, Narayanan R, Fisher SJ, Wu D, Miller DD, Dalton JT. Selective Androgen Receptor Modulator (SARM) Treatment Prevents Bone Loss and Reduces Body Fat in Ovariectomized Rats. Pharmaceutical Research, 24(2):328-335, 2006.

Bohl CE, Wu Z, Miller DD, Bell CE, Dalton JT. Crystal structure of the TS77A human androgen receptor Ugand-binding domain completed to cyproterone acetate provides insight for ligand-induced conformational changes and structure-based drug design. Journal of Biological Chemistry, 282(18):13648-13655,2007.

Gao W, Dalton JT, Expanding the therapeutic use of androgens via selective androgen receptor modulators (SARMs). Drug Discovery Today, 12(5-6):241-248, 2007.

Gao W, Dalton JT. Ockham's razor and selective androgen receptor modulators (SARMs): are we overlooking the role of 5a-reductase? Molecular Interventions, 7(1):1Q-13, 2007.

Sharifi N, Hamel E, Lill MA, Risbood P, Kane CT Jr, Hossain $MT_3$ Jones A, Dalton JT, Farrar WL. A bifunctional colchicinoid that binds to the androgen receptor. Molecular Cancer Therapeutics, 6(8):2328-2336, 2007.

Bisson WH, Chettsov $AV_5$ Bruey-Sedano N, Lin B, Chen J, Goldberger N, May LT, Christopoulos A, Dalton JT, Sexton PM, Zhang XK, Abagyan R. Discovery of antiandrogen activity of nonsteroidal scaffolds of marketed drugs. Proceedings of the National Academy of Sciences, U S A. 104(29): 1192741932, 2007.

Mukherjee A, Kirkovsky L, Marvel M, Miller DD, and Dalton JT, Development of Nonsteroidal Androgen Receptor Ligands for Imaging Prostate Tumors. PharmSci, 1(1):S-681, 1998.

Yin D, Kirkovsky L, Stourman N, Miller DD, and Dalton JT. In Vitro Pharmacology and in Vivo Pharmacokinetics Of (R)-Para-Acetamido-Bicalutamide. PharmSci, 1(4):S-3185, 1999.

Gao W, Chung K, Miller DD, and Dalton JT. In Vitro Metabolism and In Vivo Tissue Selectivity of Andarine. PharmSci 4(4): 2002.

Perera MA, Yin D, Chung K, Miller DD, and Dalton JT. Pharmacokinetics and Allometric Scaling of Andarine. PharmSci 4(4): 2002.

Xu H, Chung K, Hwang DJ, Miller $DD_7$, and Dalton JT. Pharmacodynamics of Electrophilic Androgen Receptor Ligands in Prostate Cancer Cell Lines. PharmSci 4(4): 2002.

Wang L, Miller DD, and Dalton JT, Androgen Receptor Mediated Transcriptional Activation of SARMs is Enhanced by Nuclear Receptor Coactivators. The Endocrine Society, Philadelphia, Jun. 2003, Abstract #P2-95.

Gao W, Kearbey JD, Chung K, Miller DD, and Dalton JT. Pharmacologic Effects of a Novel Selective Androgen Receptor Modulator (SARM), Flutamide and Finasteride in Intact Male Rats. The Endocrine Society, Philadelphia, Jun. 2003, Abstract #P3-221.

Kim J, Hwang DJ, Miller DD, and Dalton JT. In vitro and In vivo Pharmacologic Activity of 4-Halo Substituted SARMs. The Endocrine Society, Philadelphia, Jun. 2003, Abstract #133-198.

Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.

Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3,4-diaklyI-1,2,3,4-tetrahydro-8-pyridono[5,6-g]quinolines: potent, nonsteroidal androgen receptor agonists. Bioorg. Med. Chem. Lett., 9:1335, 1999.

Hamann LG, Mani NS, Davis RL, Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210-212, 1999.

Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38: 4855, 1995.

Dalton JT, et al "Pharmacokinetics of Aminolevulinic Acid after Oral and Intravenous Dosing in Dogs." Drug Metabolism and Disposition, 27 (4):432-435, 1999.

Grundy, Metabolic and health complications of obesity, 1990, Disease-a-Month 36:Dec; 36(12):641-731.

Halaas et al., 1995, "Weight-reducing effects of the plasma protein encoded by the obese gene", Science 269:543-546.

Hamilton et al., 1995 "Increased obese mRNA expression in omental fat cells from massively obese humans", Nature Med., 1:953.

Yepuru, et al "An Angrogen Receptor-b Specific Selective Estrogen Receptor Modulator (SERM) Inhibits the Growth of the Prostate Cancer Cells and Stromal-Epithilial Tumor Xenograft." The Endocrine Society —Programs and Abstracts —$89^{th}$ Annual Meeting —Paper OR6-3.

Kim J, Hwang DJ, Rakov I, Miller DD, and Dalton JT. Structure-Activity Relationships for Modification of the Linkage Group and B-Ring of Selective Androgen Receptor Modulators. The AAPS Journal, vol. 7(S2):T2117,2005.

Hwang DJ, Yang J, Mohler ML, Dalton JT, Miller DD.Synth.esis and testing of both reversible and irreversible selective androgen receptor modulators (SARMs) for prostate cancer. Abstracts of Papers of the American Chemical Society, 231: 274-MEDI, Mar. 26 2006.

Narayanan R, Bohl CE, Kearbey JD, Coss CC, Miller DD, and Dalton JT. Molecular Mechanism for the Tissue Selectivity of a Novel Non-Steroidal Selective Androgen Receptor Modulator: Genome-Wide Mapping of Androgen Receptor Binding Sites, the Endocrine Society, Boston, Abstract # OR49-1, Jun. 2006.

Narayanan R, Coss CC, Yepuru MM, Miller DD and Dalton JT. Steroidal Androgens and Nonsteroidal, Tissue Selective Androgen Receptor Modulators (SARM) Regulate Androgen Receptor Function Through Distinct Genomic and Non-Genomic Signaling Pathways. The Endocrine Society, Toronto, Abstract #PI-595, Jun. 2007.

Gao W, Reiser PJ, Kearbey JD, Phelps MA, Coss $CC_7$ Miller DD, and Dalton JT. Effects of a Novel Selective Androgen Receptor Modulator (SARM) on Skeletal Muscle Mass and Strength in Castrated Male Rats. The Endocrine Society, New Orleans, Abstract # P2-120, Jun. 2005.

Wu D, Wu Z, Nair V, Miller DD, and Dalton JT- Urinary Metabolites of S-I, A Novel Selective Androgen Receptor Modulator (SARM), In Rats. The AAPS Journal, vol. 6, No. 4, Abstract #W53OO, Nov. 2004.

Fisher SJ, Hong SS, Miller DD, and Dalton JT. Preclinical Pharmacology and Pharmacokinetics Of A Novel A-ring Substituted Selective Androgen Receptor Modulator (SARM) in Rats. The AAPS Journal, vol. 6, No. 4, Abstract #T2256, Nov. 2004.

Bohl CE, Chang C, Mohler M, Miller DD, Swaan PW, and Dalton JT. A Ligand-based Approach to Identify Quantitative Structure Activity Relationships for the Androgen Receptor. The AAPS Journal, vol. 6, No. 4, Abstract #W4111, Nov. 2004.

Hwang DJ, Chen JY, Kim J, Dalton JT, Miller DD. Synthesis and biological testing of (2S)-multU halogenated B-ring 2-hydroxy-2-methylpropionamide selective androgen receptor modulators (SARMs): Probing the B-ring pockets Abstracts of Papers of the American Chemical Society, 229: U140-U140 176- MEDI Part 2, Mar. 13, 2005.

Hwang DJ, Chen JY, Xu HP, Mustafa SM, Dalton JT, Miller DD. Synthesis of isothiocyanate derivatives of irreversible selective androgen receptor modulators (SARMs) and biological testing in prostate cancer cell lines. Abstracts of Papers of the American Chemical Society, 229: U140-1J140 177-MEDI Part 2, Mar. 13, 2005.

Gao W, Stuart LB, Yates CR, Miller DD, and Dalton JT. Regulation of Cytochrome P450s by Selective Androgen Receptor Modulators (SARMs) in Primary Culture of Human Hepatocytes.). PharmSci 5 (4): T3 3 3 8,2003.

Gao W Veverka KA, Chung K. Miller DD, and Dalton JT. Species Difference in the Metabolism of Selective Androgen Receptor Modulators (SARMs). PharmSci 5 (4): T3336, 2003.

Kearbey JD, Gao W, Miller DD, and Dalton JT. Selective androgen receptor modulators inhibit bone resorption in rats. PharmSci 5 (4): R6167, 2003.

Xu H, Hwang DJ, Miller DD, and Dalton JT. In Vitro and In Vivo Anticancer Activity of S-NTBA for Prostate Cancer. PharmSci 5 (4): 12378, 2003.

* cited by examiner

- $p < 0.05$; **$p<0.01$

SELECTIVE ANDROGEN RECEPTOR MODULATORS AND METHODS OF USE THEREOF

CROSS-REFERENCE TO RELATED APPLICATIONS

This application is a Continuation-In-Part Application of U.S. patent application Ser. No. 10/961,380, filed Oct. 12, 2004, which claims priority from U.S. Provisional Application Ser. No. 60/510,138, filed Oct. 14, 2003; U.S. patent application Ser. No. 10/861,923 filed Jun. 7, 2004, which is a Continuation-In-Part Application of U.S. patent application Ser. No. 10/310,150, filed Dec. 5, 2002, which claims priority of U.S. Provisional Application Ser. No. 60/336,185, filed Dec. 6, 2001; and U.S. patent application Ser. No. 10/863,524, filed Jun. 9, 2004, now abandoned, which is a Continuation-In-Part Application of U.S. patent application Ser. No. 10/371,213 filed Feb. 24, 2003, now U.S. Pat. No. 7,026,500, which is a Continuation-In-Part Application of U.S. patent application Ser. No. 10/270,232 filed Oct. 15, 2002, now U.S. Pat. No. 6,838,484, which is a Continuation-In-Part Application of U.S. patent application Ser. No. 09/935,045 filed Aug. 23, 2001, now U.S. Pat. No. 6,569,896, which claims priority of U.S. Provisional Application Ser. No. 60/300,083 filed Jun. 25, 2001 and U.S. Provisional Application Ser. No. 60/367,355 filed Aug. 24, 2000, which are hereby incorporated by reference.

GOVERNMENT INTEREST STATEMENT

This invention was made in whole or in part with government support under grant number R29 CA068096, awarded by the National Cancer Institute, National Institute of Health, and under grant number R15 HD35329, awarded by the National Institute of Child Health and Human Development, National Institute of Health. The government may have certain rights in the invention.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208-18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone(MENT): The Optimal Androgen For Male Contraception," Ann. Med., 25:199-205 (1993) ("Sundaram"). Because the AR is involved in male sexual development and function, the AR is a likely target for effecting male contraception or other forms of hormone replacement therapy.

BMD (bone mineral density decreases with age in both males and females. Decreased amounts of bone mineral content (BMC) and BMD correlate with decreased bone strength and predispose patients to fracture.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly with the aging of the population. Worldwide fracture incidence is forecasted to increase threefold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake. However, osteoporosis also occurs frequently in males. It is well established that the bone mineral density of males decrease with age. Decreased amounts of bone mineral content and density correlates with decreased bone strength, and predisposes to fracture. The molecular mechanisms underlying the pleiotropic effects of sex-hormones in non-reproductive tissues are only beginning to be understood, but it is clear that physiologic concentrations of androgens and estrogens play an important role in maintaining bone homeostasis throughout the life-cycle. Consequently, when androgen or estrogen deprivation occurs there is a resultant increase in the rate of bone remodeling that tilts the balance of resorption and formation to the favor of resorption that contributes to the overall loss of bone mass. In males, the natural decline in sex-hormones at maturity (direct decline in androgens as well as lower levels of estrogens derived from peripheral aromatization of androgens) is associated with the frailty of bones. This effect is also observed in males who have been castrated.

Muscle wasting refers to the progressive loss of muscle mass and/or to the progressive weakening and degeneration of muscles, including the skeletal or voluntary muscles, which control movement, cardiac muscles, which control the heart (cardiomyopathics), and smooth muscles. Chronic muscle wasting is a chronic condition (i.e. persisting over a long period of time) characterized by progressive loss of muscle mass, weakening and degeneration of muscle.

The loss of muscle mass that occurs during muscle wasting can be characterized by a muscle protein degradation by catabolism. Protein catabolism occurs because of an unusually high rate of protein degradation, an unusually low rate of protein synthesis, or a combination of both. Muscle protein catabolism, whether caused by a high degree of protein degradation or a low degree of protein synthesis, leads to a decrease in muscle mass and to muscle wasting.

Muscle wasting is associated with chronic, neurological, genetic or infectious pathologies, diseases, illnesses or conditions. These include Muscular Dystrophies such as Duchenne Muscular Dystrophy and Myotonic Dystrophy; Muscle Atrophies such as Post-Polio Muscle Atrophy (PPMA); Cachexias such as Cardiac Cachexia, AIDS Cachexia and Cancer Cachexia, malnutrition, Leprosy, Diabetes, Renal Disease, Chronic Obstructive Pulmonary Disease (COPD), Cancer, end stage Renal failure, Sarcopenia, Emphysema, Osteomalacia, HIV Infection, AIDS, and Cardiomyopathy.

In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism.

An intact androgen receptor (AR) signaling pathway is crucial for appropriate development of skeletal muscles. Furthermore, an intact AR-signaling pathway increases lean muscle mass, muscle strength and muscle protein synthesis.

Muscle wasting, if left unabated, can have dire health consequences. For example, the changes that occur during muscle wasting can lead to a weakened physical state that is detrimental to an individual's health, resulting in increased susceptibility to infraction and poor performance status. In addition, muscle wasting is a strong predictor of morbidity and mortality in patients suffering from cachexia and AIDS.

Innovative approaches are urgently needed at both the basic science and clinical levels to prevent and treat osteoporosis and other bone-related disorders and muscle wasting, in particular chronic muscle wasting. The present invention is directed to satisfying this need.

SUMMARY OF THE INVENTION

In one embodiment, the present invention provides, a selective androgen receptor modulator (SARM) compound or its prodrug, analog, isomer, metabolite, derivative, pharmaceutically acceptable salt, pharmaceutical product, polymorph, crystal, impurity, N-oxide, hydrate or any combination thereof, represented by a structure of formula (I):

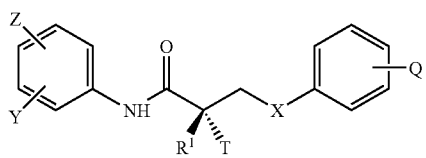

wherein
X is O;
Z is $NO_2$, CN, COR, or CONHR;
Y is I, $CF_3$, Br, Cl, F or $Sn(R)_3$;
Q is CN.
T is OH, OR, —$NHCOCH_3$, NHCOR or OC(O)R
R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$.

In another embodiment, the present invention provides a selective androgen receptor modulator (SARM) compound or its prodrug, analog, isomer, metabolite, derivative, pharmaceutically acceptable salt, pharmaceutical product, polymorph, crystal, impurity, N-oxide, hydrate or any combination thereof, represented by a structure of formula (III):

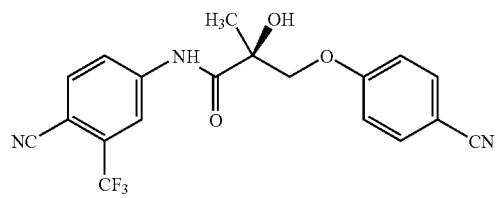

In another embodiment, this invention provides a selective androgen receptor modulator (SARM) compound or its prodrug, analog, isomer, metabolite, derivative, pharmaceutically acceptable salt, pharmaceutical product, polymorph, crystal, impurity, N-oxide, hydrate or any combination thereof, represented by a structure of formula (IV):

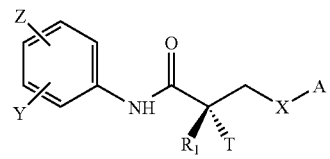

wherein
X is O;
T is OH, OR, $NHCOCH_3$, NHCOR or OC(O)R;
Z is hydrogen, alkyl, $NO_2$, CN, COOH, COR, NHCOR or CONHR;
Y is hydrogen, alkyl, $CF_3$, halogen hydroxy-alkyl or alkyl aldehyde;
A is a group selected from:

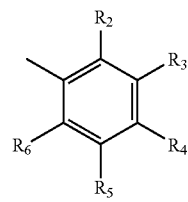

wherein
$R_2$, $R_3$, $R_4$, $R_5$, $R_6$ are independently H, halogen, CN, $NO_2$, $NHCOCF_3$;
R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$ In one embodiment, according to this aspect of the invention, X is O, or in another embodiment, T is OH, or in another embodiment, R1 is CH3, or in another embodiment, Z is $NO_2$ or in another embodiment, Z is CN, or in another embodiment, R2, R3, R5, R6 are hydrogens and R4 is $NHCOCF_3$, or in another embodiment, R2, R3, R5, R6 are hydrogens and R4 is F, or in another embodiment, R2, R3, R5, R6 are hydrogens, or in another embodiment, Z is in the para position, or in another embodiment, Y is in the meta position, or in another embodiment, any combination thereof In another embodiment, the invention provides a pharmaceutical composition comprising the SARM compounds of formula (I), (III) or (IV) and a suitable carrier or diluent.

In another embodiment, the invention provides a use of the compound of formula (I), (III) or (IV), or a composition comprising the same, in treating a subject having a bone-related disorder.

In another embodiment, the invention provides a use of the compound of formula (I), (III) or (IV) or a composition comprising the same, in increasing the strength of, or mass of a bone of a subject, or in promoting bone formation in a subject.

In another embodiment, the invention provides a use of the compound of formula (I), (III) or (IV) for treating, preventing, suppressing, inhibiting or reducing the incidence of a muscle wasting disorder in a subject.

In another embodiment, the invention provides a use of the compound of formula (I), (III) or (IV) in increasing muscle performance, muscle size, muscle strength, or any combination thereof in a subject.

In another embodiment, the invention provides a use of the compound of formula (I), (III) or (IV), or a composition comprising the same, in treating obesity or diabetes associated with a metabolic syndrome in a subject In another embodiment, the invention provides a use of the compound of formula (I), (III) or (IV), or a composition comprising the same, in promoting or speeding recovery following a surgical procedure.

In another embodiment, the invention provides a use of the compound of formula (I), (III) or (IV), or a composition comprising the same, in promoting or suppressing spermatogenesis in a male subject

DETAILED DESCRIPTION OF THE PRE, SENT INVENTION

Figure 1:
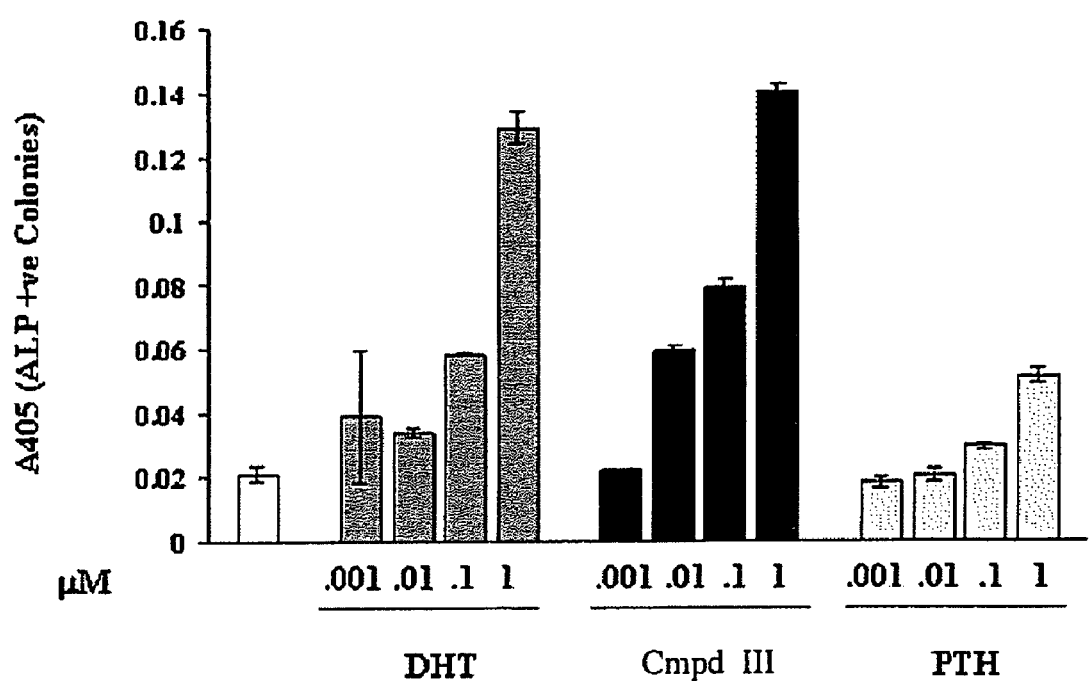
FIG. 1: Effect of SARMs, DHT and PTH on Differentiation of Rat Bone Marrow Cells Towards Osteoblast Lineage.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention In one embodiment the present invention provides, a selective androgen receptor modulator (SARM) compound or its prodrug, analog, isomer, metabolite, derivative, pharmaceutically acceptable salt, pharmaceutical product, polymorph, crystal, impurity, N-oxide, hydrate or any combination thereof, represented by a structure of formula (I):

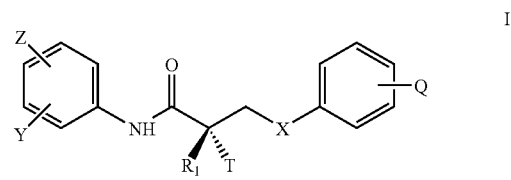

wherein
X is O;
Z is $NO_2$, CN, COR, or CONHR;
Y is I, $CF_3$, Br, Cl, F or $Sn(R)_3$;
Q is CN.
T is OH, OR, —$NHCOCH_3$, NHCOR or OC(O)R
R is alkyl, haloalkyl, dihaloalkyl, trihaloalkyl, $CH_2F$, $CHF_2$,
$CF_3$, $CF_2CF_3$, aryl, phenyl, halogen, alkenyl or OH; and
$R_1$ is $CH_3$, $CH_2F$, $CHF_2$, $CF_3$, $CH_2CH_3$, or $CF_2CF_3$ In another embodiment, the present invention provides a SARM represented by a structure of formula (II):

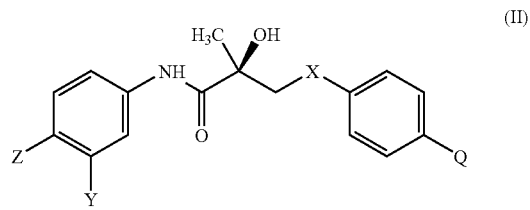

wherein
X is O;
Z is $NO_2$, CN, COR, or CONHR;
Y is I, $CF_3$, Br, Cl, F or $Sn(R)_3$;
R is an alkyl group or OH; and
Q is CN.

In one embodiment, the invention provides a selective androgen receptor modulator (SARM) compound or its prodrug, analog, isomer, metabolite, derivative, pharmaceutically acceptable salt, pharmaceutical product, polymorph, crystal, impurity, N-oxide, hydrate or any combination thereof, represented by a structure of formula (III):

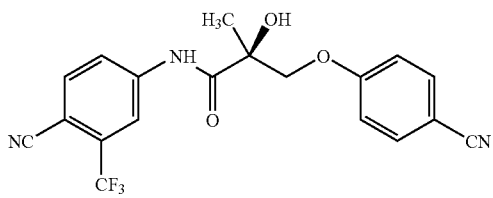

(III)

In another embodiment, this invention provides a selective androgen receptor modulator (SARM) compound or its prodrug, analog, isomer, metabolite, derivative, pharmaceutically acceptable salt, pharmaceutical product, polymorph, crystal, impurity, N-oxide, hydrate or any combination thereof, represented by a structure of formula (IV):

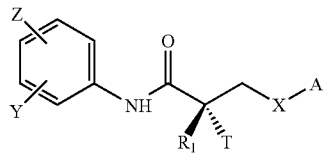

IV

Wherein

X is O;

T is OH, OR, NHCOCH$_3$, NHCOR or OC(O)R;

Z is hydrogen, alkyl, NO$_2$, CN, COOH, COR, NHCOR or CONHR;

Y is hydrogen, alkyl, CF$_3$, halogen, hydroxy-alkyl or alkyl aldehyde;

A is a group selected from:

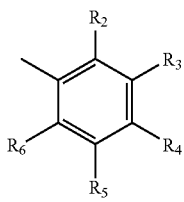

wherein $R_2$, $R_3$, $R_4$, $R_5$, $R_6$ are independently H, halogen, CN, NO$_2$, NHCOCF$_3$;

R is alkyl, haloalkyl, dihaloalkyl, trihaloalkyl, CH$_2$F, CHF$_2$, CF$_3$,

CF$_2$CF$_3$, aryl, phenyl, halogen, alkenyl or OH; and $R_1$ is CH$_3$, CH$_2$F, CHF$_2$, CF$_3$, CH$_2$CH$_3$, or CF$_2$CF$_3$.

In one embodiment, according to this aspect of the invention, X is O, or in another embodiment, T is OH, or in another embodiment, R1 is CH$_3$, or in another embodiment, Z is NO$_2$ or in another embodiment, Z is CN, or in another embodiment, R2, R3, R5, R6 are hydrogens and R4 is NHCOCF3, or in another embodiment, R2, R3, R5, R6 we hydrogens and R4 is F, or in another embodiment, R2, R3, R5, R6 are hydrogens, or in another embodiment, Z is in the para position, or in another embodiment, Y is in the meta position, or in another embodiment, any combination thereof.

In one embodiment, the invention provides a pharmaceutical composition, including compounds of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof, and a suitable carrier or diluent.

An "alkyl" group refers, in one embodiment, to a saturated aliphatic hydrocarbon, including straight-chain, branched-chain aid cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

An "alkenyl" group refers, in another embodiment, to an unsaturated hydrocarbon, including straight chain, branched chain and cyclic groups having one or more double bond. The alkenyl group may have one double bond, two double bonds, three double bonds etc. Examples of alkenyl groups are ethenyl, propenyl, butenyl, cyclohexenyl etc. The alkenyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, in one embodiment by F, in another embodiment by Cl, in another embodiment by Br, in another embodiment by 1.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. It is understood by a person skilled in the art that when T in die compounds of the present invention is OR, R is not OH.

In one embodiment, the term "halo" or "halogen refers to in one embodiment to F, in another embodiment to Cl, in another embodiment to Br, in another embodiment to I.

An "arylalkyl" group refers, in another embodiment, to an alkyl bound to an aryl, wherein alkyl and aryl are as defined above. An example of an arylalkyl group is a benzyl group.

In one embodiment, this invention provides a SARM compound and/or, analog, derivative, isomer, metabolite, pharmaceutically acceptable salt, pharmaceutical product, hydrate, N-oxide, prodrug, polymorph, impurity or crystal or combinations thereof. In one embodiment, this invention provides an analog of the SARM compound. In another embodiment, this invention provides a derivative of the SARM compound. In another embodiment, this invention provides an isomer of the SARM compound. In another embodiment, this invention provides a metabolite of the SARM compound. In another embodiment, this invention provides a pharmaceutically acceptable salt of the SARM compound. In another embodiment, this invention provides a pharmaceutical product of the SARM compound. In another embodiment, this invention provides a hydrate of the SARM compound. In another embodiment, tills invention provides an N-oxide of the SARM compound. In another embodiment, this invention provides a prodrug of the SARM compound. In another embodiment, this invention provides a polymorph of the SARM compound. In another embodiment, this invention provides a crystal of the SARM compound. In another embodiment, this invention provides an impurity of the SARM compound. In another embodiment, this invention provides composition comprising a SARM compound, as described herein, or, in another embodiment, a combination of an analog, derivative, isomer, metabolite, pharmaceutically acceptable salt, pharmaceutical product, hydrate, N-oxide, prodrug, polymorph, impurity or crystal of the SARM compounds of the present invention.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and die (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the SARMs of this invention, which may be produced, in one embodiment, using an amino-substituted SARM and an organic and inorganic acids, for example, citric acid and hydrochloric acid. Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters.

The invention also includes N-oxides of the amino substituents of the SARMs described herein.

This invention provides derivatives of the SARM compounds. In one embodiment, "derivatives" includes but is not limited to ether derivatives, acid derivatives, amide derivatives, ester derivatives and the like. In another embodiment, this invention further includes hydrates of the SARM compounds. In one embodiment, "hydrate" includes but is not limited to hemihydrate, monohydrate, dihydrate, trihydrate and the like.

This invention provides, in other embodiments, metabolites of the SARM compounds. In one embodiment, "metabolite" means any substance produced from another substance by metabolism or a metabolic process.

This invention provides, in other embodiments, pharmaceutical products of the SARM compounds. The term "pharmaceutical product" refers, in other embodiments, to a composition suitable for pharmaceutical use (pharmaceutical composition), for example, as described herein.

Selective Androgen Receptor Modulators (SARMS)

Selective androgen receptor modulators (SARMs) are a class of androgen receptor targeting agents (ARTA), which demonstrate androgenic and anabolic activity of a nonsteroidal ligand for the androgen receptor. These novel agents are useful in males for the treatment of a variety of hormone-related conditions such as sexual dysfunction, decreased sexual libido, erectile dysfunction, hypogonadism, sarcopenia, osteopenia, osteoporosis, alterations in cognition and mood, depression, anemia, hair loss, obesity, benign prostate hyperplasia and/or prostate cancer. Further, SARMs are useful for oral testosterone replacement therapy, and imaging prostate cancer. In addition, SARMs are useful in females for the treatment of a variety of hormone-related conditions including, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer.

As contemplated herein, this invention provides a class of compounds which are Selective Androgen Receptor Modulator (SARM) compounds. These compounds, which are useful in preventing and treating muscle wasting disorders and bone related disorders are classified as androgen receptor agonists (AR agonists), partial agonists or androgen receptor antagonists (AR antagonists), A receptor agonist is a substance which binds receptors and activates them. A receptor partial agonist is a substance which binds receptor and partially activate them. A receptor antagonist is a substance which binds receptors and inactivates them. As demonstrated herein, the SARM compounds of the present invention may, in some embodiments, have a tissue-selective effect, wherein, for example, a single agent is an agonist, partial agonist and/or antagonist, depending on the tissue in which the receptor is expressed. For example, the SARM compound may stimulate muscle tissue and concurrently inhibit prostate tissue. In one embodiment, the SARMs which are useful in treating and preventing muscle wasting disorders are AR agonists, and are, therefore, useful in binding to and activating the AR. In another embodiment, the SARMs are AR antagonists, and are, therefore, useful in binding to and inactivating the AR. Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds inhibit the growth of AR containing tissue.

In yet another embodiment, die SARM compounds of the present invention can be classified as partial AR agonist/antagonists. The SARMs are AR agonists in some tissues, to cause increased transcription of AR-responsive genes (e.g. muscle anabolic effect). In other tissues, these compounds serve as competitive inhibitors of testosterone/DHT on the AR to prevent agonistic effects of the native androgens. The term SARM or selective androgen receptor modulator refers, in one embodiment, to a compound which modulates androgen receptor activity. In one embodiment, the SARM is an agonist, or in another embodiment, an antagonist.

In one embodiment, the SARM will have antagonist activity in a gonad of a subject, and agonist activity peripherally, such as, for example, in muscle. Such activity was demonstrated herein, in terms of effects on prostate tissue versus that of levator ani muscle tissue, as exemplified in FIG. 3, 4 or 5.

In one embodiment, the SARM compounds of the present invention bind reversibly or, in another embodiment, irreversibly to the androgen receptor. In one embodiment, the SARM compounds bind reversibly to the androgen receptor. In another embodiment, the SARM compounds bind irreversibly to the androgen receptor. The compounds of the present invention may contain a functional group (affinity label) that allows alkylation of the androgen receptor (i.e. covalent bond formation). Thus, in this case, the compounds bind irreversibly to the receptor and, accordingly, cannot be displaced by a steroid, such as the endogenous ligands DHT and testosterone.

In one embodiment, modulation of the androgen receptor refers to the ability of the compound to stimulate or enhance signaling through the receptor, and any or, in another embodiment, all, downstream effects of receptor signal transduction.

In another embodiment, modulation of the androgen receptor refers to the ability of the compound to diminish or abrogate signaling through the receptor, and any or, in another embodiment, all, downstream effects of receptor signal transduction.

In another embodiment, a SARM of this invention may interact with a homologue of an androgen receptor. In one embodiment, the term "homologue of an androgen receptor" refers to structurally or, in another embodiment, functionally related receptors, whose regulation is desired. In one embodiment, the SARMs of this invention may interact with estrogen receptors, or, in another embodiment, other cell surface molecules which are involved in anabolic pathways, or in another embodiment, steroidogenic pathways, or in another embodiment, metabolic pathways.

In one embodiment, this invention also provides for a composition comprising a SARM, or in another embodiment, SARMs of this invention.

In one embodiment the composition is a pharmaceutical composition, which, in another embodiment is a pellet, a tablet, a capsule, micronized and non-micronized capsule, a solution, a suspension, an emulsion, an elixir, a gel, a cream, a suppository or a parenteral formulation.

In one embodiment, the micronized capsules comprise particles containing a SARM of this invention, wherein the term "micronized" used herein refers to particles having a particle size is of less than 100 microns, or in another embodiment, less than 50 microns, or in another embodiment, less than 35 microns, or in another embodiment, less than 15 microns, or in another embodiment, less than 10 microns, or in another embodiment, less than 5 microns.

The pharmaceutical compositions may be administered in any effective, convenient manner including, for instance, administration by intravascular (i.v.), intramuscular (i.m.), intranasal (i.n.), subcutaneous (s.c.), sublingual, oral, rectal, intravaginal delivery, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the compositions of this invention may include, a SARM of this invention or any combination thereof, together with one or more pharmaceutically acceptable excipients.

In one embodiment, "pharmaceutical composition" can mean a therapeutically effective amount of one or more compounds of the present invention together with suitable excipients and/or carriers useful in the methods of this invention. In one embodiment, the compositions will comprise a therapeutically effective amount of a SARM of this invention. In one embodiment, the term "therapeutically effective amount" may refer to that amount that provides a therapeutic effect for a given condition and administration regimen. In one embodiment, such compositions can be administered by any method known in the art.

In one embodiment, the compositions of the present invention are formulated as oral or parenteral dosage forms, such as uncoated tablets, coated tablets, pills, capsules, powders, granulates, dispersions or suspensions. In another embodiment, the compositions of the present invention are formulated for intravenous administration. In another embodiment, the compounds of the present invention are formulated in ointment, cream or gel form for transdermal administration. In another embodiment, the compounds of the present invention are formulated as an aerosol or spray for nasal application. In another embodiment, the compositions of the present invention are formulated in a liquid dosage form. Examples of suitable liquid dosage forms include solutions or suspensions in water, pharmaceutically acceptable fats and oils, alcohols or other organic solvents, including esters, emulsions, syrups or elixirs, solutions and/or suspensions.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

The SARMs of this invention may be administered at various dosages. In one embodiment, the SARM is administered at a dosage of 0.1-200 mg per day. In one embodiment, the SARM is administered at a dose of 0.1-10 mg, or in another embodiment, 0.1-25 mg, or in another embodiment, 0.1-50 mg, or in another embodiment, 0.3-15 mg, or in another embodiment, 0.3-30 mg, or in another embodiment, 0.5-25 mg, or in another embodiment, 0.5-50 mg, or in another embodiment, 0.75-15 mg, or in another embodiment, 0.75-60 mg, or in another embodiment, 1-5 mg, or in another embodiment, 1-20 mg, or in another embodiment, 3-15 mg, or in another embodiment, 30-50 mg, or in another embodiment, 30-75 mg, or in another embodiment, 100-2000 mg.

The SARMs of this invention may be administered at various dosages. In one embodiment, the SARM is administered at a dosage of 1 mg. In another embodiment the SARM is administered at a dosage of 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg,

In one embodiment, the compounds and compositions of this invention may be used for any of the methods of this invention, as described herein. In one embodiment, use of a SARM or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the SARM compound is being administered.

In one embodiment, this invention provides for the use of a SARM compound of this invention, or its prodrug, analog, isomer, metabolite, derivative, pharmaceutically acceptable salt, pharmaceutical product, polymorph, crystal, impurity, N-oxide, hydrate or any combination thereof, for 1) treating a bone related disorder; 2) preventing a bone related disorder; 3) suppressing a bone related disorder; 4) inhibiting a bone related disorder; 5) increasing a strength of a bone of a subject; 5) increasing a bone mass in a subject; 6) use for t osteoclastogenesis inhibition. In one embodiment the SARM compound is a compound of formula I, II, III or IV, as described herein.

In one embodiment, the bone related disorder is a genetic disorder, or in another embodiment, is induced as a result of a treatment regimen for a given disease. For example, and in one embodiment, the SARMs of this invention are useful in treating a bone-related disorder that arises as a result of androgen-deprivation therapy, given in response to prostate carcinogenesis in a subject.

In one embodiment, the present invention provides a use of SARM compound for preventing a bone-related disorder in a subject. In another embodiment, the present invention provides a use of SARM compound for suppressing a bone-related disorder in a subject. In another embodiment, the present invention provides a use of SARM compound for inhibiting a bone-related disorder in a subject. In another embodiment the SARM compound is of formula (I), (II), (III) or (IV). In another embodiment, the SARM compound is of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof.

In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty. In another embodiment, the bone-related disorder is a loss of BMD. In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures call also occur in other skeletal areas. Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

In another embodiment, the primary osteoporosis is Type I primary osteoporosis. In another embodiment, the primary osteoporosis is Type II primary osteoporosis. Each type of osteoporosis represents a separate embodiment of the present invention.

Osteoporosis and osteopenia are, in another embodiment, systemic skeletal diseases characterized by low bone mass and microarchitectural deterioration of bone tissue, "Microarchitectural deterioration" refers, in one embodiment, to thinning of the trabeculae (defined below) and the loss of inter-trabecular connections in bone. In another embodiment, "osteoporosis" is defined as having a BMD 2.5 standard deviations (SD) or more below the young adult mean. In another embodiment, "osteoporosis" is defined as having a BMC 2.5 SD or more below the young adult mean. In another embodiment, "osteoporosis" is defined as having a BMD 2.0 SD or more below the young adult mean. In another embodiment, "osteoporosis" is defined as having a BMC 2.0 SD or more below the young adult mean. In another embodiment, "osteoporosis" is defined as having a BMD 3.0 SD or more below the young adult mean. In another embodiment, "osteoporosis" is defined as having a BMC 3.0 SD or more below the young adult mean. Each definition of osteoporosis or osteopenia represents a separate embodiment of the present invention.

In another embodiment, "osteoporosis" is defined as having a BMD 2.5 SD below the young adult mean. In another embodiment, "osteoporosis" is defined as having a BMC 2.5 SD below the young adult mean. In another embodiment, "osteoporosis" is defined as having a BMD 2.0 SD below the young adult mean. In another embodiment, "osteoporosis" is defined as having a BMC 2.0 SD below the young adult mean. In another embodiment, "osteoporosis" is defined as having a BMD 3.0 SD below the young adult mean. In another embodiment, "osteoporosis" is defined as having a BMC 3.0 SD below the young adult mean. Each definition of osteoporosis represents a separate embodiment of the present invention.

Methods for assessing osteoporosis and osteopenia are well known in the art. For example, in one embodiment, a patients BMD, measured by densitometry and expressed in $g/cm^2$, is compared with a "normal value," which is the mean BMD of sex-matched young adults at their peak bone mass, yielding a "T score." In another embodiment, Z-score, the amount of bone loss in a patient is compared with the expected loss for individuals of the same age and sex. In another embodiment, "osteoporosis" is defined as having a T score 2.5 SD or more below the young adult mean. In another embodiment, "osteoporosis" is defined as having a Z score 2.5 SD or more below the young adult mean. In another embodiment, "osteoporosis" is defined as having a T score 2.0 SD or more below the young adult mean. In another embodiment, "osteoporosis" is defined as having a Z score 2.0 SD or more below the young adult mean. In another embodiment, "osteoporosis" is defined as having a T score 3.0 SD or more below the young adult mean. In another embodiment, "osteoporosis" is defined as having a Z score 3.0 SD or more below the young adult mean.

In another embodiment, "osteoporosis" is defined as having a T score 2.5 SD below the young adult mean. In another embodiment, "osteoporosis" is defined as having a Z score 2.5 SD below the young adult mean. In another embodiment, "osteoporosis" is defined as having a T score 2.0 SD below the young adult mean. In another embodiment, "osteoporosis" is defined as having a Z score 2.0 SD below the young adult mean. In another embodiment, "osteoporosis" is defined as having a T score 3.0 SD below the young adult mean. In another embodiment, "osteoporosis" is defined as having a Z score 3.0 SD below the young adult mean. Each definition of osteoporosis represents a separate embodiment of the present invention.

The term "BMD" is, in one embodiment, a measured calculation of the true mass of bone. The absolute amount of bone as measured by BMD generally correlates with bone strength and its ability to bear weight. By measuring BMD, it is possible to predict fracture risk in the same manner that measuring blood pressure can help predict the risk of stroke.

BMD, in one embodiment, can be measured by known BMD mapping techniques. In one embodiment, bone density of the hip, spine, wrist, or calcaneus may be measured by a variety of techniques. The preferred method of BMD measurement is dual-energy x-ray densitometry (DEXA). BMD of the hip, antero-posterior (AP) spine, lateral spine, and wrist can be measured using this technology. Measurement at any site predicts overall risk of fracture, but information from a specific site is the best predictor of fracture at that site. Quantitative computerized tomography (QCT) is also used to measure BMD of the spine. See for example, "Nuclear Medicine: "Quantitative Procedures" by Wahner H W, et al, published by Toronto Little, Brown & Co., 1983, pages 107-132; "Assessment of Bone Mineral Part 1," J Nucl Medicine, pp 1134-1141 (1984); and "Bone Mineral Density of The Radius" J Nucl Medicine 26: 13-39 (1985). Each method of measuring BMD represents a separate embodiment of the present invention.

"Osteopenia" refers, in one embodiment, to having a BMD or BMC between 1 and 2.5 SD below the young adult mean. In another embodiment, "osteopenia" refers to decreased calcification or density of bone. This term encompasses, in one embodiment, all skeletal systems in which such a condition is noted. Each definition or means of diagnosis of the disorders disclosed in the present invention represents a separate embodiment of die present invention.

In one embodiment, the term "bone fracture" refers to a breaking of bones, and encompasses both vertebral and non-vertebral bone fractures. The term "bone frailty" refers, in one embodiment, to a weakened state of the bones that predisposes them to fractures.

In one embodiment, the bone-related disorder is treated with a SARM compound of this invention, or a combination thereof. In another embodiment, other bone-stimulating compounds can be provided to a subject, prior to, concurrent with or following administration of a SARM or SARMs of this invention. In one embodiment, such a bone stimulating compound may comprise natural or synthetic materials.

In one embodiment, the bone stimulating compound may comprise a bone morphogenetic protein (BMP), a growth factor, such as epidermal growth factor (EGF), a fibroblast growth factor (FGF, a transforming growth factor (TGF-α or TGF-β), an insulin growth factor (IGF), a platelet-derived growth factor (PDGF) hedgehog proteins such as sonic, indian and desert hedgehog, a hormone such as follicle stimulating hormone, parathyroid hormone, parathyroid hormone related peptide, activins, inhibins, frizzled, frzb or frazzled proteins, BMP binding proteins such as chordin and fetuin, a cytokine such as IL-3, IL-7, GM-CS F, a chemokine, such as eotaxin, a collagen, osteocalcin, osteonectin and others, as will be appreciated by one skilled in the art.

In another embodiment, the compositions for use in treating a bone disorder of this invention may comprise a SARM or SARMs of this invention, an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblast.

In another embodiment, nucleic acids which encode bone-stimulating compounds may be administered to the subject, which is to be considered as part of this invention.

In one embodiment, the osteoporosis, osteopenia, increased bone resorption, bone fracture, bone frailty, loss of BMD, and other diseases or disorders of the present invention are caused by a hormonal disorder, disruption or imbalance. In another embodiment, these conditions occur independently of a hormonal disorder, disruption or imbalance. Each possibility represents a separate embodiment of the present invention.

In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is Luteinizing Hormone (LH). In another embodiment, the hormone is Follicle Stimulating Hormone (FSH). In another embodiment, the hormone is any other hormone known in the art. In another embodiment, the hormonal disorder, disruption or imbalance is associated with menopause. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject.

Each possibility represents a separate embodiment of the present invention.

In one embodiment, the invention provides a use of SARM compounds for increasing a strength of a bone of a subject. In another embodiment the SARM compound is of formula (I), (II), (III) or (IV). In another embodiment, the SARM compound is of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof. Thus, increasing a strength of a bone of a subject.

In another embodiment, the subject has an osteoporosis. In another embodiment the osteoporosis is hormonally induced.

In one embodiment, the invention provides a use of SARM compounds for increasing a bone mass of a subject. In another embodiment the SARM compound is of formula (I), (II), (III) or (IV). In another embodiment, the SARM compound is of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, the subject has osteoporosis. In another embodiment the osteoporosis is hormonally induced. In another embodiment the subject has sarcopenia or cachexia. In another embodiment the methods of this invention provide for increasing a bone mass in the subject, which is a cortical bone mass. In another embodiment the bone mass is trabecular bone mass. In another embodiment the bone mass is a cancellous bone mass.

In one embodiment, the invention provides a use of SARM compounds for promoting bone formation. In another embodiment the SARM compound is of formula (I), (II), (III) or (IV). In another embodiment, the SARM compound is of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, the SARM compound stimulates or enhances osteoblastogenesis. In another embodiment, the said SARM compound inhibits osteoclast prolification.

In one embodiment, the invention provides for bone formation via osteoblast stimulation or enhanced proliferation. In one embodiment, die term "osteoblast" refers to cell which participates in bone-formation. In one embodiment, osteoblast involvement in bone formation may form the tissue and deposit minerals therein, giving bone its strength. In another embodiment, the invention provides for bone formation via suppression of osteoclast induction, or in another embodiment, activity. In one embodiment, the term "osteoclast" refers to a cell which participates in bone remodeling, and in particular in bone resorption.

In one embodiment, bone diseases or disorders are treated by the methods of this invention via stimulation of bone formation. In another embodiment, the treatments of this invention provide for maintenance of bone mass. Bone mass is maintained by a balance between the activity of osteoblasts that form bone and osteoclasts that break it down. In one embodiment, the compounds and methods of this invention provide a means whereby such a balance is maintained.

Figure 2:
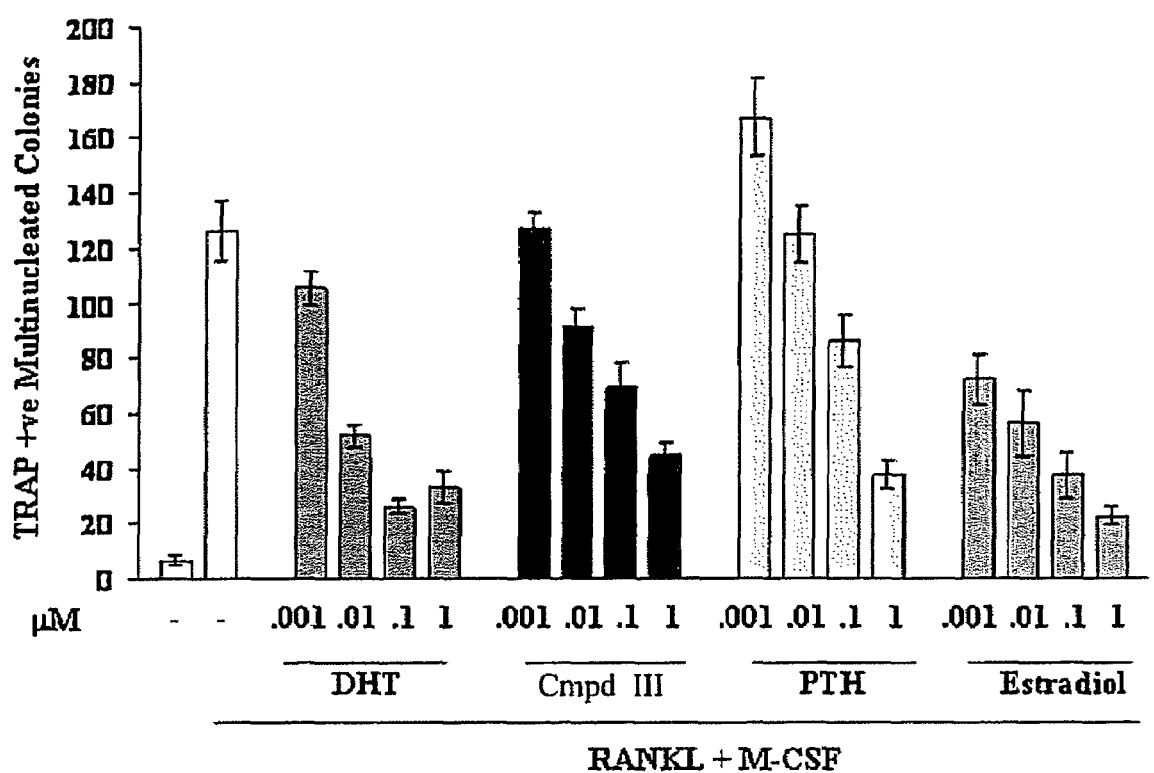
FIG. 2: Effect of SARMs, DHT and PTH on TRAP Positive Multinucleated Osteoclasts

FIGS. 1-2 demonstrate that SARM compound III induced differentiation of bone marrow cells to osteoblasts yet inhibited osteoclast induction, indicating direct effects of SARMs on both osteoblasts and osteoclasts, which would be useful in increasing bone mass in osteoporotic patients.

In one embodiment, this invention provides use of a SARM compound of this invention, or its prodrug, analog, isomer, metabolite, derivative, pharmaceutically acceptable salt, pharmaceutical product, polymorph, crystal, impurity, N-oxide, hydrate or any combination thereof, for 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder. In one embodiment the SARM compound is a compound of formula (I), (II), (III), or (IV), as described herein. In another embodiment, the invention provides a composition comprising a SARM of this invention for use in the methods as described herein.

In one embodiment, the invention provides a use of SARM compounds for treating a subject suffering from a muscle wasting disorder. In another embodiment the SARM compound is of formula (I), (II), (III), or (IV). In another embodiment, the SARM compound is of formula (I), (II), (III), or (IV) or its prodrug, analog, isomer, metabolite, derivative, pharmaceutically acceptable salt, pharmaceutical product, polymorph, crystal, impurity, N-oxide, hydrate or any combination thereof, or a composition comprising the same. Thus, treating a subject suffering from a muscle wasting disorder.

In another embodiment, the use of a SARM compound for treating a subject suffering from a muscle wasting disorder includes administering a pharmaceutical composition including the SARM compound. In another embodiment, the administering step includes intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

A muscle is a tissue of die body that primarily functions as a source of power. There are three types of muscles in the body: a) skeletal muscle—the muscle responsible for moving extremities and external areas of the bodies; b) cardiac muscle—the heart muscle; and c) smooth muscle—the muscle that is in the walls of arteries and bowel.

A wasting condition or disorder is defined herein as a condition or disorder that is characterized, at least in part, by an abnormal, progressive loss of body, organ or tissue mass. A wasting condition can occur as a result of a pathology such as, for example, cancer, or an infection, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass aid to muscle wasting. The term "catabolism" has its commonly known meaning in the art, specifically ail energy burning form of metabolism.

Muscle wasting can occur as a result of a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

In one embodiment, muscle wasting in a subject is a result of the subject having a muscular dystrophie; muscle atrophy; X-linked spinal-bulbar muscular atrophy (SBMA), cachexia; malnutrition, tuberculosis, leprosy, diabetes, renal disease, chronic obstructive pulmonary disease (COPD), cancer, end stage renal failure, sarcopenia, emphysema, osteomalacia, or cardiomyopathy.

In another embodiment, the muscle wasting disorder is due to infection with enterovirus, Epstein-Barr virus, herpes zoster, HIV, trypanosomes, influenze, coxsackie, rickettsia, trichinella, schistosoma or mycobacteria.

The muscular dystrophies are genetic diseases characterized by progressive weakness and degeneration of the skeletal or voluntary muscles that control movement. The muscles of the heart and some other involuntary muscles are also affected in some forms of muscular dystrophy. The major forms of muscular dystrophy (MD) are: duchenne muscular dystrophy, myotonic dystrophy, duchenne muscular dystrophy, becker muscular dystrophy, limb-girdle muscular dystrophy, facioscapulhumeral muscular dystrophy, congenital muscular dystrophy, oculopharyngeal muscular dystrophy, distal muscular dystrophy and emery-dreifuss muscular dystrophy.

Muscular dystrophy can affect people of all ages. Although some forms first become apparent in infancy or childhood, others may not appear until middle age or later. Duchenne MD is the most common form, typically affecting children. Myotonic dystrophy is the most common of these diseases in adults.

Muscle atrophy (MA) is characterized by wasting away or diminution of muscle and a decrease in muscle mass. For example, Post-Polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in adulthood. Because the primary disease cause is an androgen receptor mutation, androgen replacement is not a current therapeutic strategy. There are some investigational studies where exogenous testosterone propionate is being given to boost the levels of androgen with hopes of overcoming androgen insensitivity and perhaps provide an anabolic effect. Still, use of supraphysiological levels of testosterone for supplementation will have limitations and other potentially serious complications.

Cachexia is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass.

Cachexia is also seen in acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting. Studies have shown that in patients suffering injuries, chronic illnesses, burns, trauma or cancer, who are hospitalized for long periods of time, there is a long-lasting unilateral muscle wasting, with a consequent decrease in body mass.

Injuries or damage to the central nervous system (CNS) are also associated with muscle wasting disorders. Injuries or damage to the CNS can be, for example, caused by diseases, trauma or chemicals. Examples are central nerve injury or damage, peripheral nerve injury or damage and spinal cord injury or damage.

In another embodiment, muscle wasting may be a result of alcoholism, and may be treated with the compounds and compositions of the invention, representing embodiments thereof.

In one embodiment, the invention provides a use of SARM compounds for preventing a muscle wasting disorder in a subject. In another embodiment the SARM compound is of formula (I), (II), (III) or (IV). In another embodiment, the SARM compound is of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof. In another embodiment, the administering comprises administering a pharmaceutical composition comprising said SARM and/or its prodrug, analog, derivative, isomer, metabolite, pharmaceutically acceptable salt, pharmaceutical product, hydrate, N-oxide, or any combination thereof; and a pharmaceutically acceptable carrier. Thus, preventing a muscle wasting disorder in a subject.

In one embodiment, the invention provides a use of SARM compounds for treating a muscle-wasting conditions associated with chronic illness. In another embodiment the SARM compound is of formula (I), (II), (III) or (IV). In another embodiment, the SARM compound is of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof, or a composition comprising the same. In another embodiment, the use of the SARM compounds is orally administered to said subject.

In one embodiment, the present invention provides a use of a SARM compound for preventing a muscle wasting disorder in a subject, in another embodiment, suppressing a muscle wasting disorder in a subject, in another embodiment inhibiting a muscle wasting disorder in a subject, in another embodiment reducing the incidence of a muscle wasting in a subject. In another embodiment the SARM compound is of formula (I), (II), (III) or (IV). In another embodiment, the SARM compound is of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, this invention provides for the use of a SARM compound of this invention, or its prodrug, analog, isomer, metabolite, derivative, pharmaceutically acceptable salt, pharmaceutical product, polymorph, crystal, impurity, N-oxide, hydrate or any combination thereof, or a composition comprising the same, in treating, preventing, suppressing, inhibiting or reducing the incidence of a muscle wasting disorder in a subject.

In another embodiment, this invention provides for the use of a SARM of this invention, or its prodrug, analog, isomer, metabolite, derivative, pharmaceutically acceptable salt, pharmaceutical product, polymorph, crystal, impurity, N-oxide, hydrate or any combination thereof, or a composition comprising the same, in increasing muscle performance, muscle size, muscle strength, or any combination thereof in a subject.

In another embodiment, the SARMs and compositions of this invention are useful in promoting or speeding recovery following a surgical procedure.

In one embodiment, the present invention provides a use of a SARM compound for reducing a fat mass in a subject. In another embodiment the SARM compound is of formula (I), (II), (III) or (IV). In another embodiment, the SARM compound is of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, this invention provides for the use of a SARM compound of this invention, such as one having the structure of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof, or a composition comprising the same, in treating obesity or diabetes associated with a metabolic syndrome in a subject In another embodiment, the subject has a hormonal imbalance, disorder, or disease. In another embodiment the subject has menopause In one embodiment, the present invention provides a use of a SARM compound for increasing a lean mass in a subject. In another embodiment the SARM compound is of formula (I), (II), (III) or (IV). In another embodiment, the SARM compound is of formula (I), (II), (III) or (IV) or its prodrug, analog, isomer, metabolite, derivative, pharmaceutically acceptable salt, pharmaceutical product, polymorph, crystal, impurity, N-oxide, hydrate or any combination thereof. Thus, increasing a lean mass in a subject.

In another embodiment the subject has a hormonal imbalance, disorder, or disease. In another embodiment the subject has menopause.

FIGS. 3-7 demonstrate that Compound III is anabolic yet minimally androgenic, thus such compounds may be useful in treating patient groups in which androgens were contraindicated in the past. Compound III was shown to stimulate muscle growth, whether in the presence or absence of testosterone while exerting anti-proliferative effects on the prostate, thus, in one embodiment, the SARMs of this invention restore lost muscle mass in patients with sarcopenia or cachexia.

In one embodiment, the SARMs of this invention are administered intravenously, via injecting the pharmaceutical composition in liquid form to the subject. In another embodiment, the SARMs of this invention are administered intra-arterially, via injecting the pharmaceutical composition in liquid form to the subject. In another embodiment, the SARMs of this invention are administered intramuscularly via injecting the pharmaceutical composition in liquid form to the subject. In another embodiment, the SARMs of this invention are administered subcutaneously via implanting a pellet containing the pharmaceutical composition in the subject. In another embodiment the SARMs of this invention are administered orally via administering the pharmaceutical composition in a liquid or solid form to the subject. In another embodiment the SARMs of this invention are administered topically via applying the pharmaceutical composition to the skin surface of the subject.

The present invention provides, in one embodiment, a safe and effective method for treating, preventing, suppressing, inhibiting or reducing loss of muscle and/or muscle protein catabolism due to muscle wasting. The invention is useful, in another embodiment, in treating a subject suffering from a muscle wasting disorder, or in another embodiment in treating a bone related disorder. In one embodiment, the subject is a mammalian subject.

In another embodiment, this invention relates to a method of preventing, suppressing, inhibiting or reducing the incidence of obesity in a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the incidence of obesity in the subject.

In one embodiment, the SARM compounds of the present invention alter the levels of leptin in a subject. In another embodiment, the SARM compounds decrease the levels of leptin. In another embodiment, the SARM compounds of the present invention increase the levels of leptin in a subject. Leptin is known to have an effect on appetite on weight loss in obese mice, and thus has been implicated in obesity.

The SARMs of this invention, in one embodiment, affect circulating, or in another embodiment, tissue levels of leptin. In one embodiment, the term 'level/s of leptin' refers to the serum level of leptin. As contemplated herein, the SARM compounds of the present invention have an effect on leptin in-vitro and in-vitro. Leptin levels can be measured by methods known to one skilled in the art, for example by commercially available ELISA kits. In addition, Leptin levels may be determined in in-vitro assays, or in in-vivo assays, by any method known to a person skilled in the art.

Since leptin is implicated in controlling appetite, weight loss, food intake, and energy expenditure, modulating and/or controlling the levels of leptin is a useful therapeutic approach in treating preventing, inhibiting or reducing the incidence of obesity in subjects suffering from obesity. Modulating the level of leptin can result in a loss of appetite, a reduction of food intake, and an increase in energy expenditure in the subject, and thus may contribute to the control and treatment of obesity.

The term "obesity" is defined, in one embodiment, as an increase in body weight beyond the limitation of skeletal and physical requirement, as the result of excessive accumulation of fat in the body.

The term "obesity-associated metabolic disorder" refers, in one embodiment, to a disorder which results from, is a consequence of, is exacerbated by or is secondary to obesity. Non-limiting examples of such a disorder are osteoarthritis, Type II diabetes mellitus, increased blood pressure, stroke, and heart disease.

The term "osteoarthritis" refers, in another embodiment, to a non-inflammatory degenerative joint disease occurring chiefly in older people, characterized by degeneration of the articular cartilage, hypertrophy of bones and the margins and changes in the synovial membrane. It is accompanied, in other embodiments, by pain and stiffness, particularly after prolonged activity.

The term "diabetes", in one embodiment, refers to a relative or absolute lack of insulin leading to uncontrolled carbohydrate metabolism. Most patients can be clinically classified as having either insulin-dependent diabetes mellitus (IDDM or Type-I diabetes) or non-insulin-dependent diabetes mellitus (NIDDM or Type-II diabetes).

The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage.

The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In addition, androgens have recently been shown to be involved in commitment of mesenchymal pluripotent cells into myogenic lineage and to block differentiation into adipogenic lineage (Singh et al., Endocrinology, 2003, Jul. 24). Accordingly, selective androgen receptor modulator compounds can be useful in methods of blocking adipogenesis, and/or altering stem cell differentiation, as described herein.

In another embodiment, this invention relates to a method of promoting, increasing or facilitating weight loss in a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to promote, increase or facilitate weight loss in the subject.

In another embodiment, this invention relates to a method of decreasing, suppressing, inhibiting or reducing appetite of a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the appetite of the subject.

In another embodiment, this invention relates to a method of altering the body composition of a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to alter the body composition of the subject. In one embodiment, altering the body composition comprises altering the lean body mass, the fat free body mass of the subject, or a combination thereof.

In another embodiment, this invention relates to a method of altering lean body mass or fat free body mass of a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to alter the lean body mass or fat flee body mass of the subject.

In another embodiment, this invention relates to a method of converting fat to lean muscle in a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to convert fat to lean muscle in the subject.

In another embodiment, this invention relates to a method of treating an obesity-associated metabolic disorder in a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in all amount effective to treat the obesity-associated metabolic disorder in the subject.

In another embodiment, this invention relates to a method of preventing, suppressing, inhibiting or reducing an obesity-associated metabolic disorder in a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the obesity-associated metabolic disorder in the subject.

In one embodiment, the obesity-associated metabolic disorder is hypertension. In another embodiment, the disorder is osteoarthritis. In another embodiment, the disorder is Type II diabetes mellitus. In another embodiment, the disorder is increased blood pressure. In another embodiment, the disorder is stroke. In another embodiment, the disorder is heart disease.

In another embodiment, this invention relates to a method of decreasing, suppressing, inhibiting or reducing adipogenesis in a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce adipogenesis in the subject.

In another embodiment, this invention relates to a method of altering stem cell differentiation in a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to alter stem cell differentiation in the subject.

In another embodiment, this invention relates to a method of altering the level of leptin in a subject, comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, in an amount effective to alter the level of leptin in the subject. In one embodiment, altering the level of leptin comprises decreasing the level of leptin in the subject.

In another embodiment, this invention relates to a method of decreasing, suppressing, inhibiting or reducing the level of leptin in a subject, comprising the step of administering to the subject a selective androgen receptor modulator (SARM) of this invention and/or its analog, derivative, isomer metabolite, pharmaceutically acceptable salt, pharmaceutical product, hydrate, N-oxide, prodrug, polymorph, crystal, or any combination thereof, in an amount effective to decrease, suppress, inhibit or reduce the level of leptin in the subject.

In one embodiment, the SARM that is useful in a) treating, preventing, suppressing, inhibiting, or reducing obesity; b) promoting, increasing or facilitating weight loss; c) decreasing, suppressing, inhibiting or reducing appetite; d) altering the body composition; e) altering lean body mass or fat free body mass; f) converting fat to lean muscle; g) treating, preventing, suppressing, inhibiting, or reducing an obesity-associated metabolic disorder, for example hypertension, osteoarthritis, Type II diabetes mellitus, increased blood pressure, stroke, or heart disease; h) decreasing, suppressing, inhibiting or reducing adipogenesis; i) altering stem cell differentiation; and/or j) altering the level of leptin, is a compound represented by the structure of formula (I), (II), (III) or (IV).

In one embodiment, the SARMs of this invention find utility in treating or halting the progression of, or treating symptoms of diabetes. In another embodiment, the SARMs of this invention are useful in treating co-morbidities related to diabetes. These conditions include: hypertension, cerebrovascular disease, atherosclerotic coronary artery disease, macular degeneration, diabetic retinopathy (eye disease) and blindness, cataracts—systemic inflammation (characterized by elevation of inflammatory markers such as erythrocyte sedimentation rate or C-reactive protein), birth defects, pregnancy related diabetes, pre-ecclampsia and hypertension in pregnancy, kidney disease (renal insufficiency, renal failure etc.), nerve disease (diabetic neuropathy), superficial and systemic fungal infections, congestive heart failure, gout/hyperuricemia, obesity, hypertriglyceridemia, hypercholesterolemia, fatty liver disease (non-alcoholic steatohepatitis, or NASH), and diabetes-related skin diseases such as Necrobiosis Lipoidica Diabeticorum (NLD), Blisters of diabetes (Bullosis Diabeticorum), Eruptive Xanthomatosis, Digital Sclerosis, Disseminated Granuloma Annulare, and Acanthosis Nigricans.

In one embodiment this invention provides a method for a) treating, preventing, suppressing inhibiting atherosclerosis b) treating, preventing, suppressing inhibiting liver damage due to fat deposits comprising the step of administering to the subject a selective androgen receptor modulator (SARM) of this invention and/or its analog, derivative, isomer, metabolite, pharmaceutically acceptable salt, pharmaceutical product, hydrate, N-oxide, prodrug, polymorph, crystal, or any combination thereof, or a composition comprising the same, in an amount effective to treat, prevent or inhibit atherosclerosis and liver damage due to fat deposit.

In one embodiment, the SARM that is useful in a) treating, preventing, suppressing, inhibiting, or reducing atherosclerosis; b) treating, preventing, suppressing inhibiting liver damage due to fat deposits.

In one embodiment atherosclerosis refers to a slow, complex disease that may begin with damage to the innermost layer of the artery. In another embodiment the causes of damage to the arterial wall may include a) elevated levels of cholesterol and in the blood; b) high blood pressure; c) tobacco smoke d) diabetes. In another embodiment, the condition is treatable in a smoker, despite the fact that tobacco smoke may greatly worsen atherosclerosis and speed its growth in the coronary arteries, the aorta and arteries in the legs. Similarly, in another embodiment, the methods of this invention may be useful in treating subjects with a family history of premature cardiovascular disease who have an increased risk of atherosclerosis.

In one embodiment, liver damage due to fat deposits refer to the build-up of fat in the liver cells forming a Fatty Liver which may be associated with or may lead to inflammation of the liver. This can cause scarring and hardening of the liver. When scarring becomes extensive, it is called cirrhosis. In another embodiment the fat accumulates in the liver as obesity. In another embodiment fatty liver is also associated with diabetes mellitus, high blood triglycerides, and the heavy use of alcohol. In another embodiment fatty Liver may occur with certain illnesses such as tuberculosis and malnutrition, intestinal bypass surgery for obesity, excess vitamin A in the body, or the use of certain drugs such as valproic acid (trade names: Depakene/Depakote) and corticosteroids (cortisone, prednisone). Sometimes fatty liver occurs as a complication of pregnancy In one embodiment, the methods of use in treating a subject are where the subject is a human, and in another embodiment, where the subject is male, or in another embodiment, where the subject is female.

In another embodiment, this invention provides for the use of a SARM of this invention, or a composition comprising the same, in promoting or suppressing spermatogenesis in a male subject. Some of the SARMs of the present invention exhibit, inter-alia, androgenic activity, which in turn stimulates spermatogenesis. In other embodiments, the SARMs of this invention exhibit antagonist activity in the gonads of a subject, which in turn, may suppress spermatogenesis. In one embodiment, the SARMs may therefore be used as a contraceptive.

It is to be understood that any use of the SARMs of this invention, including, inter-alia, uses in applications regarding diseases or conditions which pertain to muscle, fat, cardiac, liver, gonadal or bone tissue, whereby administration of the SARM compounds of this invention, or a composition comprising the same, alter the course of such diseases or conditions favorably for a subject, ale to be considered as part of this invention.

The following examples are presented in order to more fully illustrate the preferred embodiments of the invention. They should in no way, however, be construed as limiting the broad scope of the invention.

EXAMPLES

Example 1

Effects of Selective Androgen Receptor Modulator (SARM) compound III on Progenitor Cell Differentiation To Osteoblasts and Osteoclasts Materials and Methods Chemicals Compound III, THT and PTH were prepared at concentrations ranging from 1 nM-1 µM.

Animals

Four month old female rats were sacrificed by euthanasia and the femurs were excised from the animals. The femurs were cleaned off any muscle and connective tissues and were stored on ice in Minimum Essential Medium (MEM) with penicillin, Streptomycin and Fungizone until the cells were cultured.

Bone Marrow Cell Culture

All cell culture materials were obtained from Invitrogen (Carlsbad, Calif.). The femurs were first rinsed in 70% ethanol and were washed three times with 5 ml each of penicillin and streptomycin. Both the ends of the femurs were snapped and the bone marrow cells were flushed with 15 ml of MEM with penicillin, Streptomycin and Fungizone into a 50 ml conical tube and stored on ice. The same procedure was performed with all the femurs. The bone marrow cells and were pooled were centrifuged at 1000 rpm for 5 min in a clinical centrifuge. The cells were resuspended in MEM without phenol red supplemented with 10% charcoal stripped serum, penicillin, streptomycin and fungizone. The cells were triturated through a 22 g needle, counted under microscope and were plated at 1.5 million cells per well of a 6 well plate in MEM without phenol red supplemented with 15% charcoal stripped serum, penicillin streptomycin, 300 ng/ml fungizone, 0.28 mM Ascorbic acid and 10 mM β-glycerophosphate to differentiate towards fibroblast/osteoblast lineage and at 2.5 million cells per well of a 24 well plate in MEM without phenol red supplemented with 10% charcoal stripped serum, penicillin streptomycin and 300 ng/ml fungizone to differentiate towards osteoclast lineage. The medium was changed on day 2 and the cells were treated with the indicated hormone. Osteoclast cultures were carried out in the presence of 50 ng RANK Ligand and 10 ng GM-CSF to induce osteoclastogenesis. Medium was completely changed every third day for osteoclast cultures. For fibroblast cultures, half the culture medium was changed every third day to leave the growth factors secreted by the cells.

Staining of Cells

At the end of 12 days, the cells were fixed in 10% buffered formalin for fibroblast cultured and in 4% formaldehyde in PBS for osteoclast cultures. The fibroblasts were stained for alkaline phosphatase activity and the O.D. at 405 nm was measured using a spectrophotometer as described earlier. Osteoclasts were stained for Tartarate Resistant Acid Phosphatase Activity (TRAP) and cells having 2 or more nuclei were counted under the microscope and plotted as indicated earlier.

Results

SARMs are Potent Inducers of Differentiation of Bone Marrow Cells Towards the Osteoblast and Osteoclast Lineage Androgens exert anabolic effects on bone and lack of androgens under conditions such as androgen deprivation therapy in prostate cancer and in old age have clearly indicated the benefits of androgens as a bone protective hormone. However; the use of ectopic androgen is limited due to its side effects and also due to the risk of conversion of androgens to estrogens.

In order to determine whether a SARM could be therapeutic yet obviate the above side-effects, various selective androgen receptor modulators (SARMs) were evaluated in terms of their ability to have bone protective effects, with fewer side effects, as seen with the parent hormone. The efficacy of Di-hydro testosterone (DHT) and Parathyroid hormone (PTH) were compared to a SARM, Compound III in terms of their ability to differentiate primary rat bone marrow cells towards the osteoblast and the osteoclast lineage (FIGS. 1 and 2). Bone marrow cells from rats were cultured in the presence or absence of the above indicated hormones for 12 days in culture medium and were evaluated in terms of their differentiation towards osteoblast or osteoclast lineage.

DHT and Compound III all increased differentiation of primary bone marrow cells toward the osteoblast lineage as measured by alkaline phosphatase (ALP) activity of the cells (FIG. 1). At 1 μM concentration, DHT and the SARM induced the ALP activity comparably whereas at lower concentrations of 100 nM and 10 nM Compound III showed better induction than the DHT. PTH, another bone anabolic hormone induced the ALP staining only at higher concentration but not at lower concentrations.

FIG. 2 shows a clear increase in the number of TRAP positive multinucleated osteoclasts, when cells were incubated in the presence of RANK ligand and GM-CSF. Treatment of cells with DHT or SARM significantly inhibited RANK ligand and GM-CSF-induced TRAP positive multinucleated osteoclast proliferation. PTH inhibited induction at higher concentrations, however, at lower concentrations, PTH increased the number of TRAP positive osteoclasts. Estradiol inhibited osteoclastogenesis, at all dosages evaluated.

Example 2

SARM Bone Effects Alone and in Combination With the Anti-Resorptive Agent, Alendronate Materials and Methods Sixty female, virgin, intact Sprague-Dawley rats were obtained from Charles River Laboratories (Wilmington, Mass.) and aged to 23 wks. The animals were housed 2-3 per cage and acclimated to a 12-h light/dark cycle. Food (7012C LM-485 Mouse/Rat Sterilizable Diet, Harlan Teklad, Madison, Wis.) and water were provided ad libitum. The Institutional Animal Care and Use Committee of the University of Tennessee reviewed and approved the animal protocol for this study.

Sham surgeries or ovariectomies were performed on Day 0. The study was comprised of six treatment groups as follows: (1) intact+vehicle, (2) intact+COMPOUND III, (3) OVX+ vehicle, (4) OVX+COMPOUND III, (5) OVX+alendronate (6) OVX+alendronate+COMPOUND III. Doses (200 □L) were administered daily via oral gavage in a vehicle of DMSO:PEG300 (10:90) beginning on Day 1. Animals were sacrificed on Day 45 of the study. Femurs were removed, cleared of soft tissue, and stored in saline soaked gauze at −20° C. until analysis. Nine animals died during the course of the study. These deaths were attributed to surgical complications arising from the ovariectomies and technical errors during oral dosing (i.e., dosing solution delivered into the lungs). Dose groups are listed in Table 1.

TABLE 1

| | Treatment groups | | | |
|---|---|---|---|---|
| Group | Gonadal Status | Treatment | Dose | Animals/ group |
| 1 | Intact | Vehicle | N/A | 9 |
| 2 | Intact | COMPOUND III | 3 mg/day | 9 |

TABLE 1-continued

Treatment groups

| Group | Gonadal Status | Treatment | Dose | Animals/ group |
|---|---|---|---|---|
| 3 | OVX | Vehicle | N/A | 7 |
| 4 | OVX | COMPOUND III | 3 mg/day | 8 |
| 5 | OVX | Alendronate | 1 mg/day | 10 |
| 6 | OVX | Alendronate + COMPOU | 1 mg/day + 3 mg/day | 8 |

The left femurs were sent to SkeleTech Inc. (Bothell, Wash.) for biomechanical strength (three point bending) and pQCT analysis. A Stratec XCT RM and associated software (Stratec Medizintechnik GmbH, Pforzheim, Germany. Software version 5.40 C) were used for the pQCT analysis. The femur was analyzed at both the mid-shaft and distal regions. The mid-shaft analysis was performed on the region at 50% of the length of the femur. The distal analysis was performed on the region at 20% of the length of the femur starting at the distal end. One 0.5 mm slice perpendicular to the long axis of the femur was used for analysis. Total bone mineral content, total bone area, total bone mineral density, cortical bone mineral content, cortical bone area, cortical bone mineral density, cortical thickness, periosteal perimeter (circumference) and endosteal perimeter were determined at the mid-shaft of the femur. At the distal femur, total bone mineral content, total bone area, total bone mineral density, trabecular bone mineral content, trabecular bone area and trabecular bone mineral density were determined. Following pQCT analysis, the femoral strength was determined by a three-point bending test. The anterior to posterior diameter (APD) (unit:mm) at the midpoint of the femoral shaft was measured with an electronic caliper. The femur was placed on the lower supports of a three-point bending fixture with the anterior side of the femur facing downward in an Instron Mechanical Testing Machine (Instron 4465 retrofitted to 5500)(Canton, Mass.). The length (L) between the lower supports was set to 14 mm. The upper loading device was aligned to the center of the femoral shaft. The load was applied at a constant displacement rate of 6 mm/min until the femur broke. The mechanical testing machine directly measured the maximum load ($F_u$) (unit:N), stiffness (S) (units:N/mm), and energy absorbed (W) (unit:mJ). The axial area moment of inertia (I) (unit: $mm^4$) was calculated by the software during the pQCT analysis of the femoral mid-shaft. Stress ($\square$) (units:$N/mm^2$), elastic modulus (E) (unit:Mpa), and toughness (T) (units:$mJ/m^3$) were calculated by the following formulas: stress: $\square = (F_u * L * (a/2))/(4*I)$; elastic modulus: $E = S*L^3/(48*I)$; and toughness: $T = 3*W*(APD/2)^2/(L*I)$.

Statistical analysis was performed by Student's T-test. P-values of less than 0.05 were considered as statistically significant differences.

Results

Figure 3:
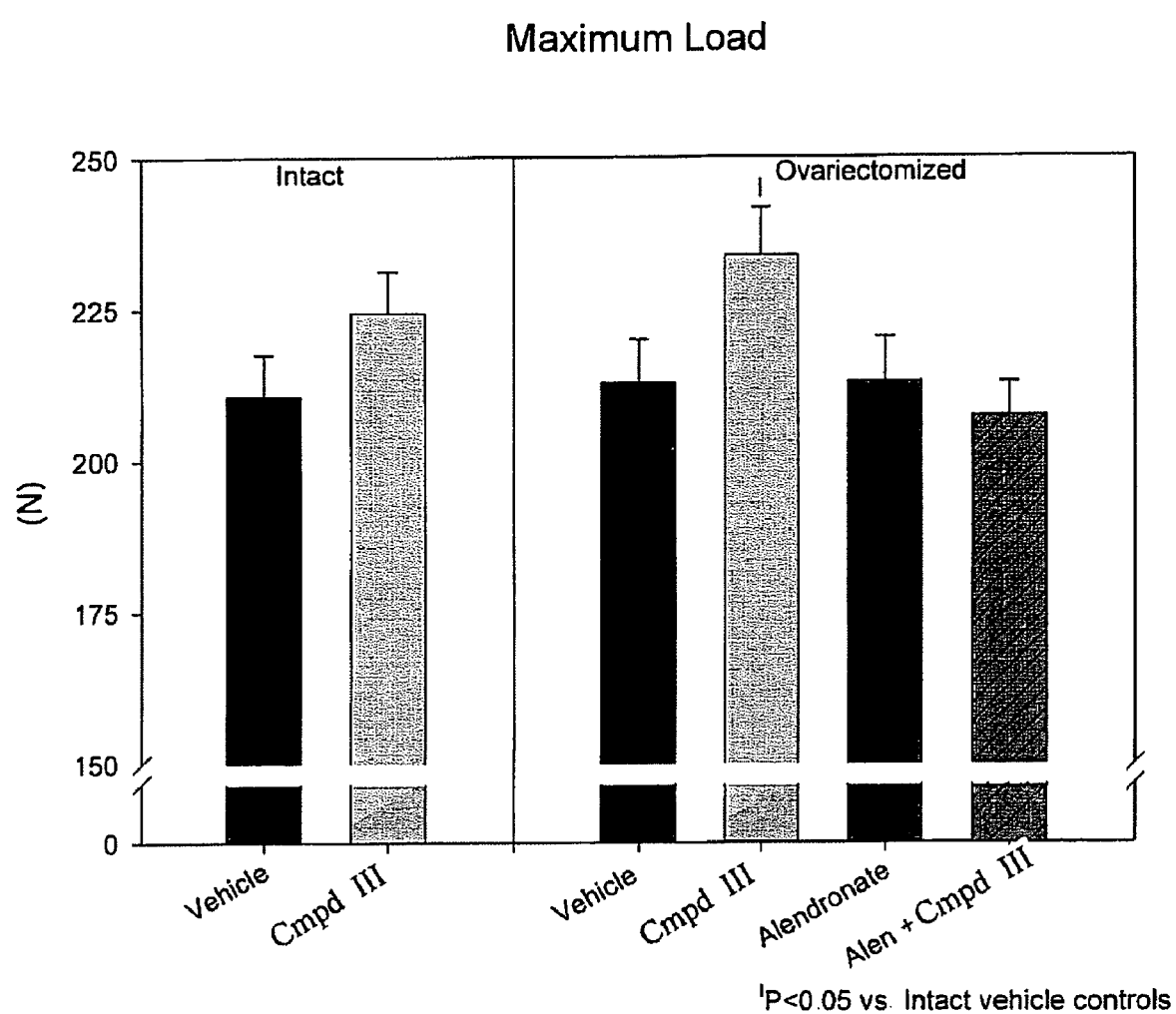
FIG. 3: Femoral maximum load determined by 3-point bending of the femur.

Femoral maximum load was determined by 3-point bending of the femur. Results are shown in FIG. 3. No differences were observed between the intact vehicle (210 N) and the OVX vehicle (212 N) control groups. We observed trends in the COMPOUND III treated groups with maximum load increasing to 224 and 233 newtons in the intact and OVX groups, respectively. The alendronate (213 N) and alendronate+COMPOUND III (207N) groups were not different from controls.

Figure 4:
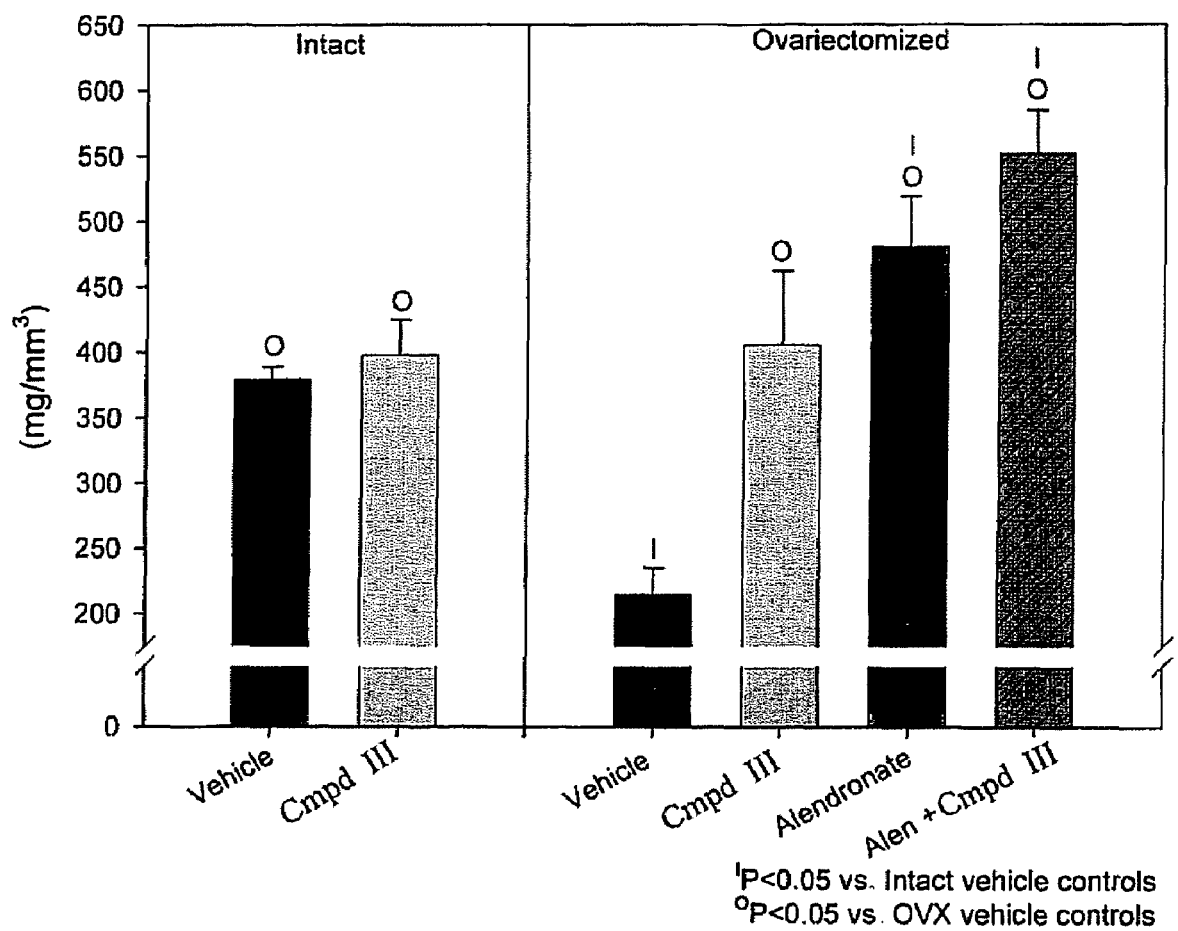
FIG. 4: Trabecular bone mineral density determined by pQCT analysis of the distal femur.

Trabecular bone mineral density was analyzed by pQCT at the distal femur. Results are shown in FIG. 4. We observed significant trabecular bone loss following OVX. Trabecular bone density decreased from 379 to 215 $mg/mm^3$ in the intact and OVX vehicle control groups, respectively. In intact animals treated with COMPOUND III, we observed a slight increase in trabecular bone density to 398 $mg/mm^3$. In OVX animals treated with COMPOUND III, we observed a significant increase over the OVX vehicle control group to 406 $mg/mm^3$. Alendronate increased trabecular bone density to 480 $mg/mm^3$. The combination therapy of Alendronate and COMPOUND III showed additive effects increasing trabecular bone density to 552 $mg/mm^3$.

Example 3

Androgenic & Anabolic Activity in Intact and ORX Rats

Materials and Methods

Male Sprague-Dawley rats weighing approximately 200 g were purchased from Harlan Bioproducts for Science (Indianapolis, Ind.). The animals were maintained on a 12-h light/dark cycle with food (7012C LM-485 Mouse/Rat Sterilizable Diet, Harlan Teklad, Madison, Wis.) and water available ad libitum. The animal protocol was reviewed and approved by the Institutional Animal Care and Use Committee of the University of Tennessee. Anabolic and androgenic activity of Compound III in intact animals was evaluated, and the dose response in acutely orchidectomized (ORX) animals was evaluated as well. Regenerative effects of Compound III in chronically (9 days) ORX rats was also assessed.

The compound was weighed and dissolved in 10% DMSO (Fisher) diluted with PEG 300 (Acros Organics, NJ) for preparation of the appropriate dosage concentrations. The animals were housed in groups of 2 to 3 animals per cage. Intact and ORX animals were randomly assigned to one of seven groups consisting of 4 to 5 animals per group. Control groups (intact and ORX) were administered vehicle daily. Compound III was administered via oral gavage at doses of 0.01, 0.03, 0.1, 0.3, 0.75, and 1 mg/day to both intact and ORX groups.

Castrated animals (on day one of the study) were randomly assigned to dose groups (4-5 animals/group) of 0.01, 0.03, 0.1, 0.3, 0.75, and 1 mg/day, for dose-response evaluation. Dosing began nine days post ORX and was administered daily via oral gavage for fourteen days. The animals were sacrificed under anesthesia (ketamine/xyalzine, 87:13 mg/kg) after a 14-day dosing regimen, and body weights were recorded. In addition, ventral prostate, seminal vesicles, and levator ani muscle were removed, individually weighed, normalized to body weight, and expressed as a percentage of intact control. Student's T-test was used to compare individual dose groups to the intact control group. Significance was defined a priori as a P-value<0.05. As a measure of androgenic activity, ventral prostate and seminal vesicle weights were evaluated, whereas levator ani muscle weight was evaluated as a measure of anabolic activity. Blood was collected from the abdominal aorta, centrifuged, and sera were frozen at −80° C. prior to determination of serum hormone levels. Serum luetinizing hormone (LH) and follicle stimulating hormone (FSH) concentrations were determined by the University of Virginia Center for Research in Reproduction Ligand Assay and Analysis Core (NICHD (SC-CPRR) Grant U54-HD28934).

Results

Figure 5:
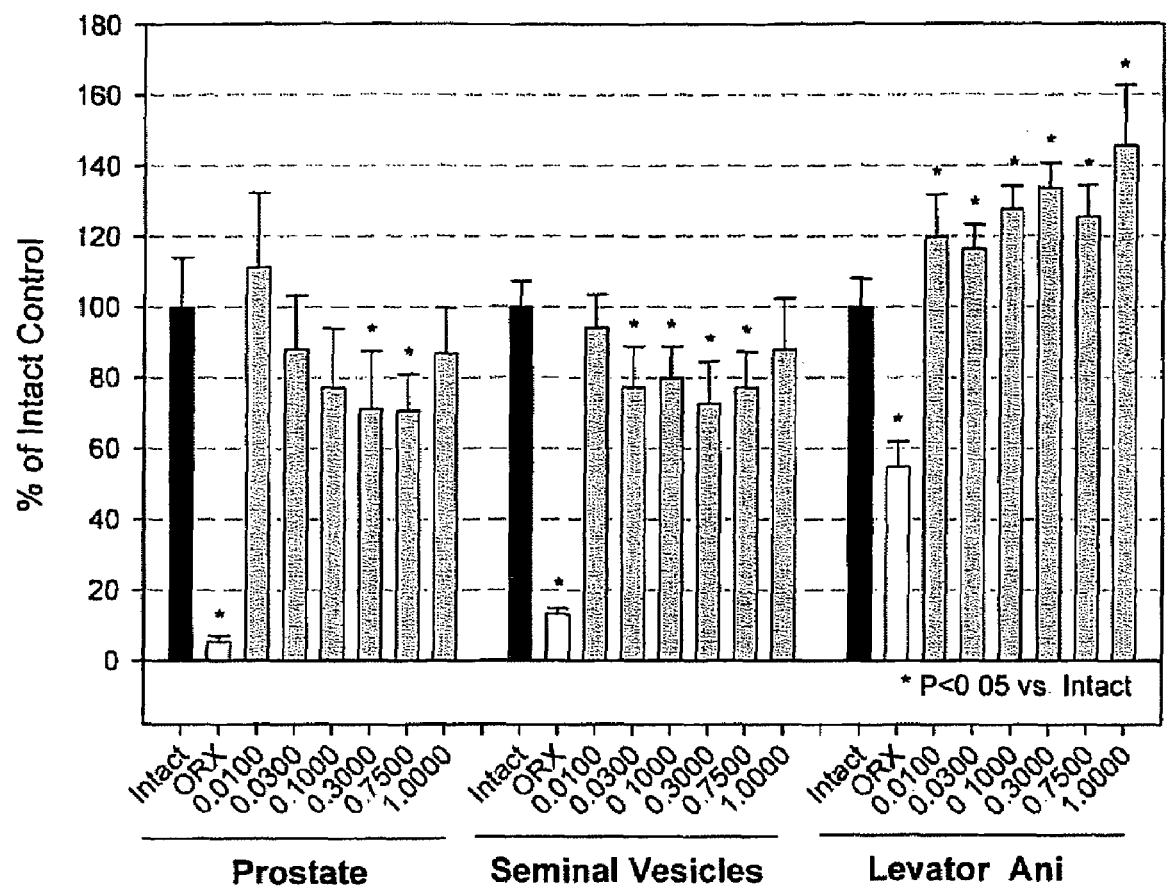
FIG. 5: Pharmacology of compound III in intact rats.
Figure 6:
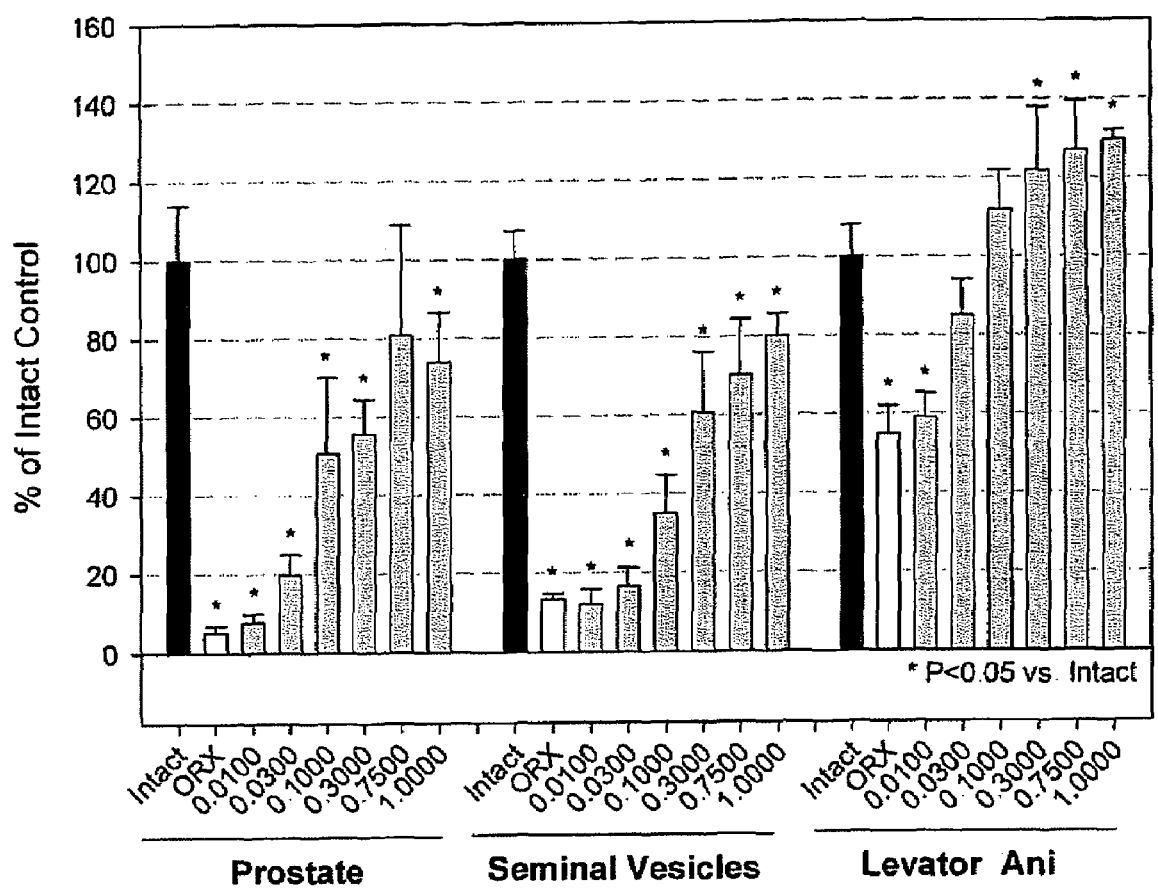
FIG. 6: Organ weights from castrated, compound III-treated rats presented as a percentage of intact control. * P-value<0.05 versus intact controls.
Figure 7:
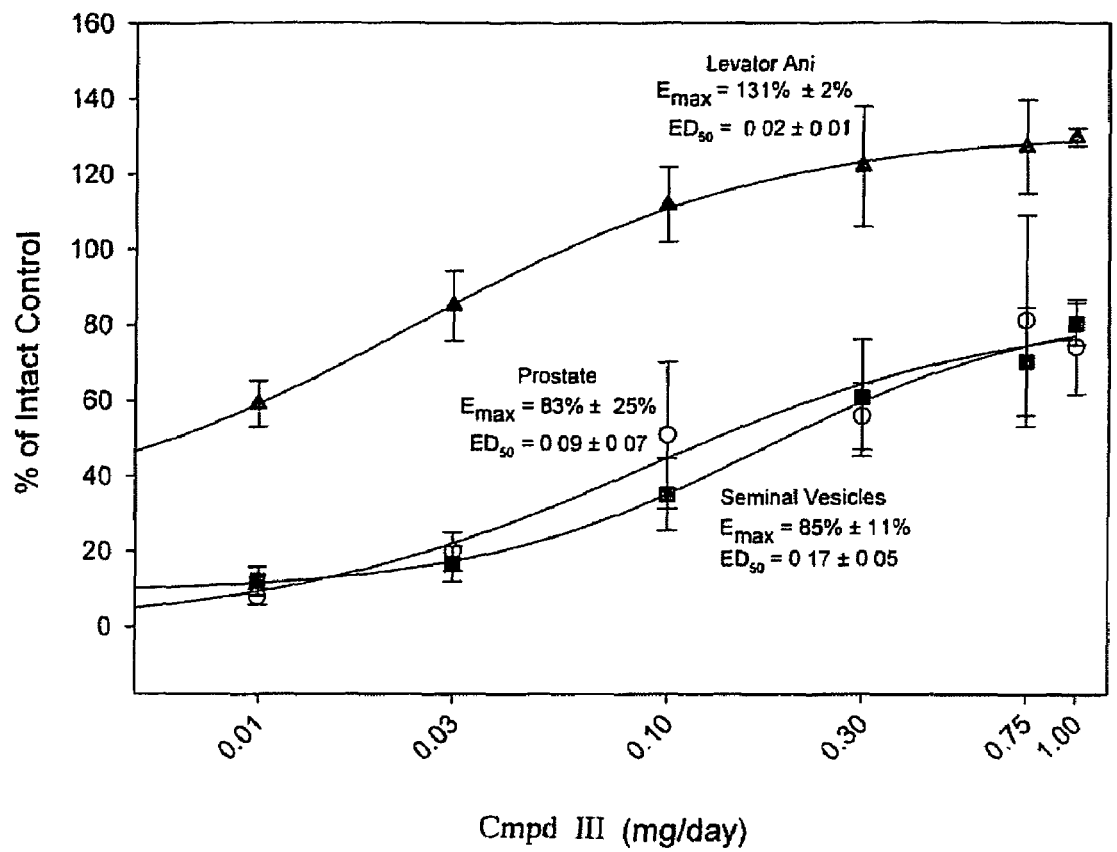
FIG. 7: Organ weight maintenance dose-response curves for compound III in castrated rats. $E_{max}$ and $ED_{50}$ values for the levator ani (closed triangles), prostate (open circles), and seminal vesicles (closed squares) were obtained by nonlinear regression analysis using the sigmoid $E_{max}$ model in WinNonlin®.

Prostate weights following Compound III treatment were 111%±21%, 88%±15%, 77%±17%, 71%±16%, 71%±10%, and 87%±13% of intact controls following doses of 0.01, 0.03, 0.1, 0.3, 0.75, and 1 mg/day, respectively (FIG. 5). Similarly, seminal vesicle weights decreased to 94%±9%, 77% 11%, 80%±9%, 73%±12%, 77%±10%, and 88%±14% of intact controls following doses of 0.01, 0.03, 0.1, 0.3, 0.75, and 1 mg/day, respectively. Significant increases were seen in levator ani muscle weights of sham animals, however, in all dose groups, when compared to intact controls. The levator ani muscle weights were 120%±12%, 116%±7%, 128%±7%, 134%±7%, 125%±9%, and 146%±17% of intact controls corresponding to 0.01, 0.03, 0.1, 0.3, 0.75, and 1.0 mg/day dose groups, respectively. The results are presented graphically in FIG. 5.

Compound III partially maintained prostate weight following orchidectomy. Prostate weight in vehicle treated ORX controls decreased to 5%±1% of intact controls. At doses of 0.01, 0.03, 0.1, 0.3, 0.75, and 1.0 mg/day, Compound III maintained prostate weights at 8%±2%, 20%±5%, 51%±19%, 56%±9%, 80%±28%, and 74±12.5% of intact controls, respectively. In castrated controls, seminal vesicle weight decreased to 13%±2% of intact controls. Compound III partially maintained seminal vesicle weights in ORX animals. Seminal vesicle weights from drug treated animals were 12%±4%, 17%±5%, 35%±10%, 61%±15%, 70%±14%, and 80%±6% of intact controls, following doses of 0.01, 0.03, 0.1, 0.3, 0.75, and 1.0 mg/day, respectively. In ORX controls the levator ani muscle weight decreased to 55%±7% of intact controls. We observed an anabolic effect in the levator ani muscle of Compound III treated animals. Compound III fully maintained levator ani muscle weights at doses>0.1 mg/day. Doses>0.1 mg/day resulted in significant increases in levator ani weight compared to that observed in intact controls. Levator ani muscle weights as a percentage of intact controls were 59%±6%, 85%±9%, 112%±10%, 122%±16%, 127±12%, and 129.66±2% for the 0.01, 0.03, 0.1, 0.3, 0.75, and 1.0 mg/day dose groups, respectively. Results are graphically presented in FIG. 6. $E_{max}$ and $ED_{50}$ values were determined in each tissue by nonlinear regression analysis in WinNonlin® and presented in FIG. 7. $E_{max}$ values were 83%±25%, 85%±11%, and 131%±2% for prostate, seminal vesicles, and levator ani, respectively. The $ED_{50}$ in prostate, seminal vesicles, and levator ani was 0.09±0.07, 0.17±0.05, and 0.02±0.01 mg/day, respectively.

Serum Hormone Analysis

Serum LH and FSH data for the animals are presented in Table 1. LH decreased in a dose-dependent manner in both intact and castrated animals. Following doses>0.1 mg/day, LH levels were below the limit of quantitation (0.07 ng/mL). The 0.1 mg/day dose in ORX animals returned LH levels back to those seen in intact controls. Similar effects were observed with FSH. In intact animals, a significant decrease in FSH levels was observed with the 0.75 and 1 mg/day doses. In ORX animals, a dose-dependent decrease in FSH levels was observed. Doses of Compound III>0.1 mg/day in ORX animals returned FSH levels to those of intact controls.

TABLE 1

Serum LH and FSH levels from animals in Arm 1 and Arm2.

| Compound III (mg/day) | Luetinizing Hormone | | Follicle Stimulating Hormone | |
|---|---|---|---|---|
| | Intact (ng/ml) | ORX (ng/ml) | Intact (ng/ml) | ORX (ng/ml) |
| Vehicle | 0.281 ± 0.126[a] | 9.66 ± 1.13[a] | 6.40 ± 1.58[b] | 43.45 ± 4.9 |
| 0.01 | 0.195 ± 0.106[a] | 8.45 ± 2.44[a] | 5.81 ± 0.31[b] | 36.23 ± 7.7 |
| 0.03 | 0.176 ± 0.092[b] | 4.71 ± 1.72 | 5.74 ± 0.78[b] | 40.15 ± 3.33[a] |
| 0.1 | 0.177 ± 0.056[b] | 0.778 ± 0.479[b] | 6.60 ± 1.08[b] | 20.69 ± 3.52[a,b] |
| 0.3 | <LOQ | <LOQ | 5.32 ± 1.80[b] | 8.73 ± 2.25[b] |
| 0.75 | <LOQ | <LOQ | 4.30 ± 0.62[a,b] | 7.19 ± 1.11[b] |
| 1 | <LOQ | <LOQ | 4.38 ± 0.42[a,b] | 6.33 ± 0.70[b] |

[a]$P < 0.05$ vs. Intact Controls.
[b]$P < 0.05$ vs. ORX Controls

Androgenic & Anabolic Activity Following Delayed Dosing

Figure 8:
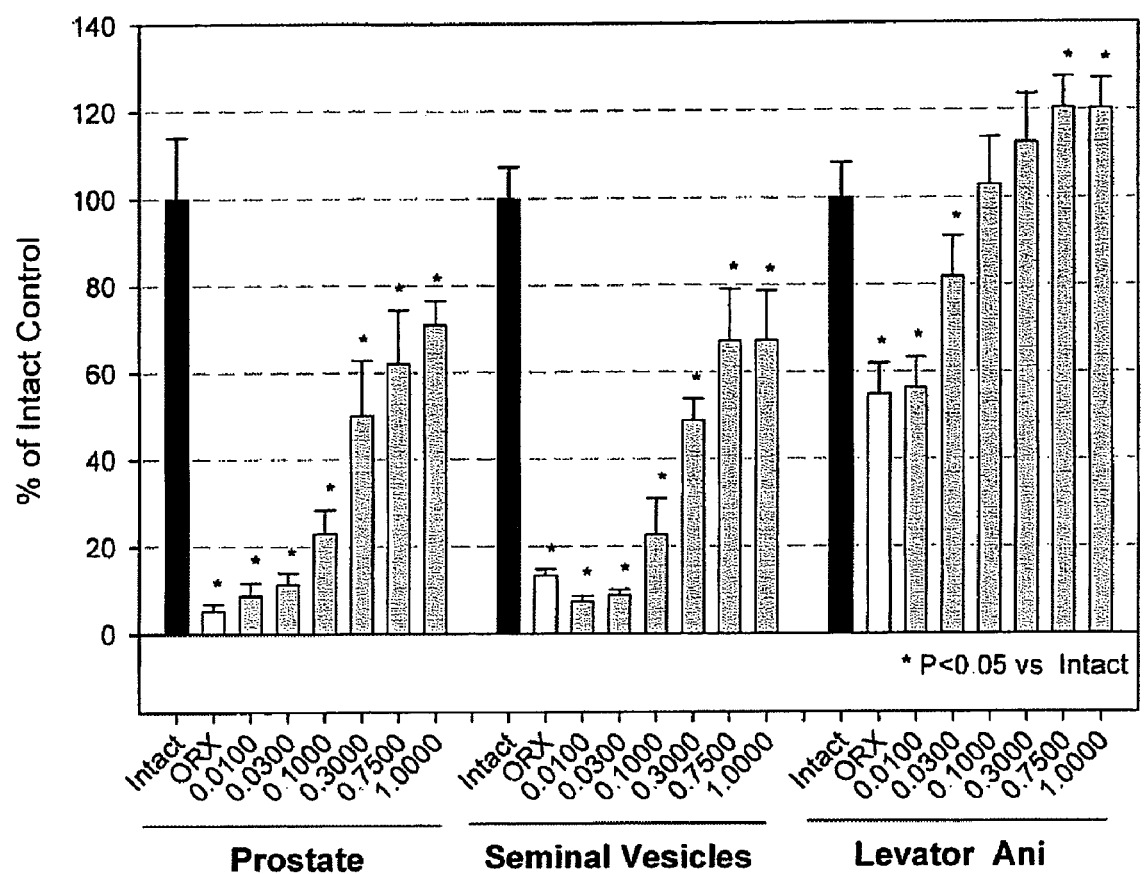
FIG. 8: Organ weights from castrated, Compound III-treated rats presented as a percentage of intact control. * P-value<0.05 versus intact controls.
Figure 9:
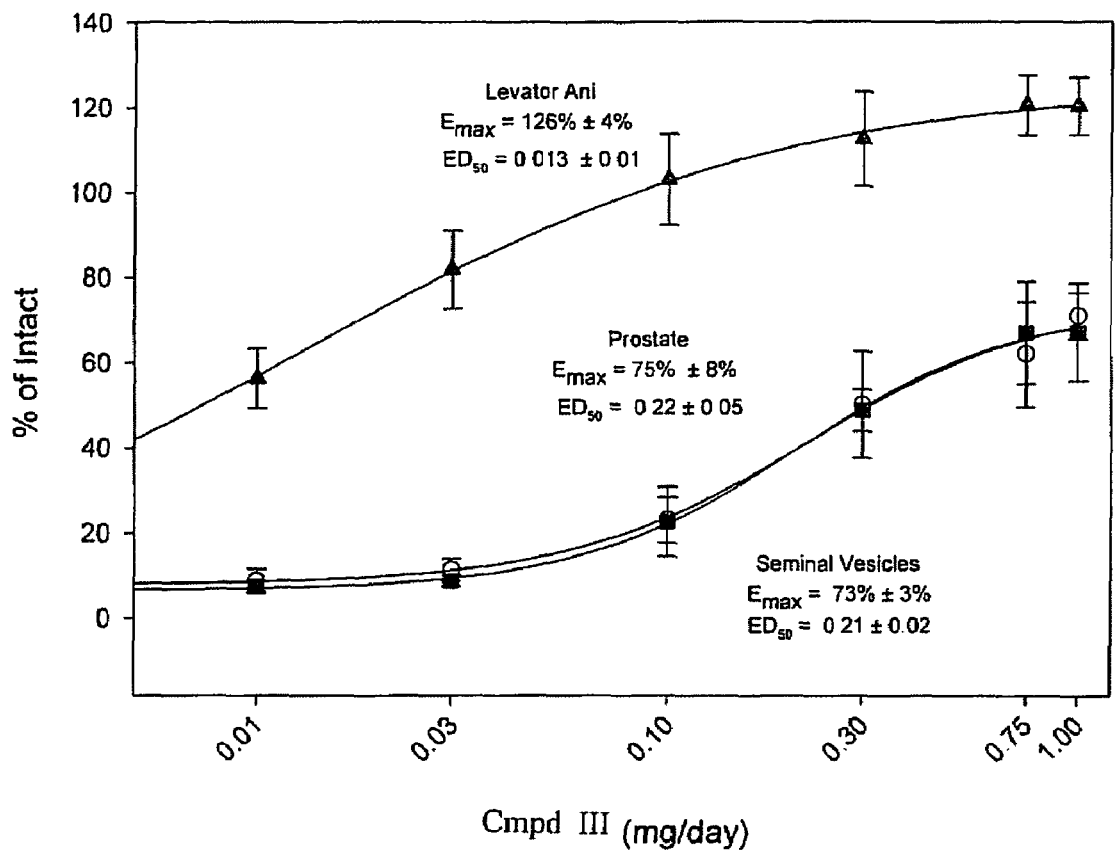
FIG. 9: Organ weight regrowth dose-response curves for compound III in castrated rats. $E_{max}$ and $ED_{50}$ values for the levator ani (closed triangles), prostate (open circles), and seminal vesicles (closed squares) were obtained by nonlinear regression analysis using the sigmoid $E_{max}$ model in WinNonlin®.

Compound III partially restored both prostate and seminal vesicle weight in ORX animals. Prostates were restored to 9%±3%, 11%±3%, 23%±5%, 50%±13%, 62%±12%, and 71%±5%, while seminal vesicles were restored 7%±1%, 9%±1%, 23%±8%, 49%±5%, 67%±12%, and 67%±11% of intact controls for the 0.01, 0.03, 0.1, 0.3, 0.75, and 1.0 mg/day dose groups, respectively. Compound III fully restored levator ani muscle weight at doses>0.1 mg/day. Levator ani muscle weights were restored to 56%±7%, 82%±9%, 103%±11%, 113%±11%, 121%±7%, and 120%±7% corresponding to doses of 0.01, 0.03, 0.1, 0.3, 0.75, and 1.0 mg/day, respectively. Results are presented graphically in FIG. 8. $E_{max}$ and $ED_{50}$ values were determined in each tissue by nonlinear regression analysis in WinNonlin® and presented in FIG. 9. $E_{max}$ values were 75%±8%, 73%±3%, and 126%±4% for prostate, seminal vesicles, and levator ani, respectively. The $ED_{50}$ in prostate, seminal vesicles, and levator ani was 0.22±0.05, 0.21±0.02, and 0.013±0.01 mg/day, respectively.

Example 4

Pharmacokinetic Characterization of the Novel Oral Anabolic SARM Compound III: The First Analysis in Healthy Male Volunteers Materials and Methods Cohorts of a maximum of 12 healthy male volunteers were dosed at each dose level (9 active, 3 placebo) in a randomized, double-blind study design. Eight cohorts were recruited (aged 18-45 years) and each cohort received one single oral dose corresponding to either 1, 3, 10, 30 or 100 mg compound III (or placebo of equal volume of PE(G300) in solution, or 3 or 30 mg in experimental capsules. The effect of micronization (i.e. particle size reduction) was investigated on the pharmacokinetics of compound III in the 30 mg solid oral dosage form. Samples for pharmacokinetic assessment of parent drug were taken for up to 72 hours following dosing.

Results

Figure 10:
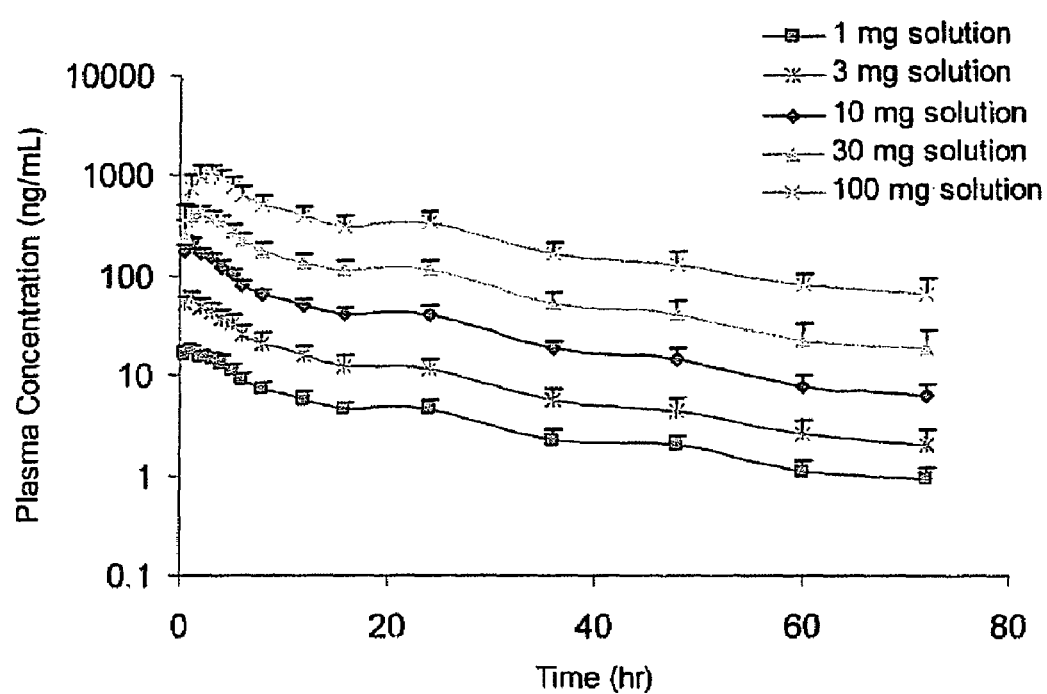
FIG. 10: Plasma concentration-time profile for compound III in healthy human volunteers with oral dose in PEG300.
Figure 11:
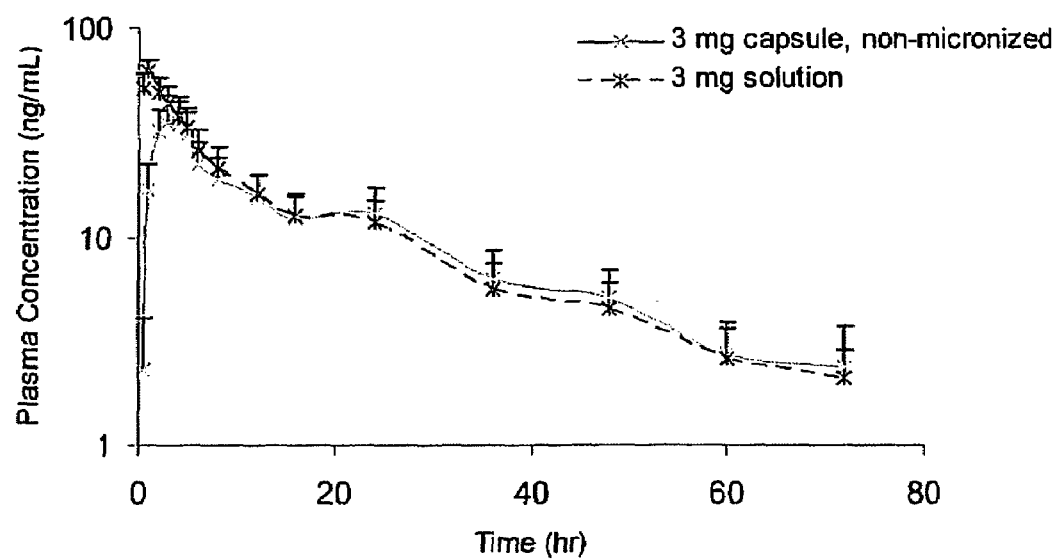
FIG. 11: Plasma-concentration-time profiles of compound III solution vs. solid oral dosage forms.
Figure 12:
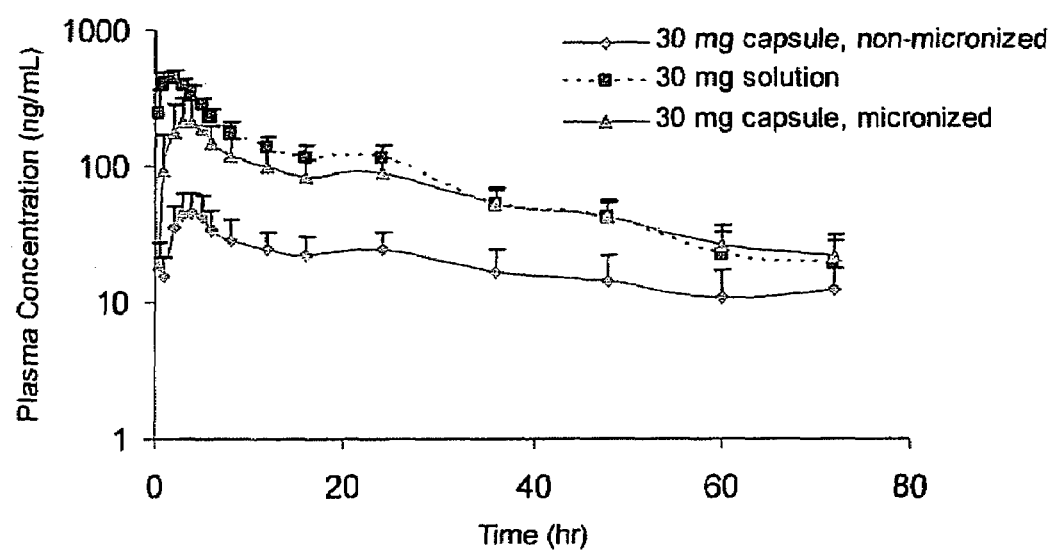
FIG. 12: Plasma-concentration-time profiles of various compound III dosage forms at 30 mg.
Figure 13:
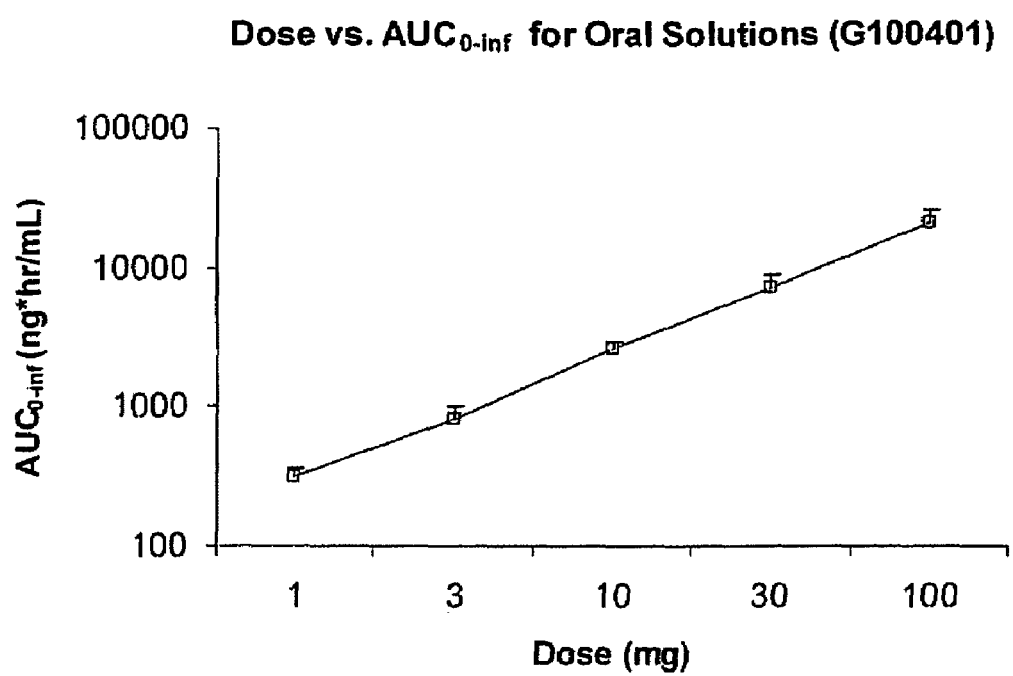
FIG. 13: Dose versus $AUC_{0-inf}$ for oral solutions (G100401)
Figure 14:
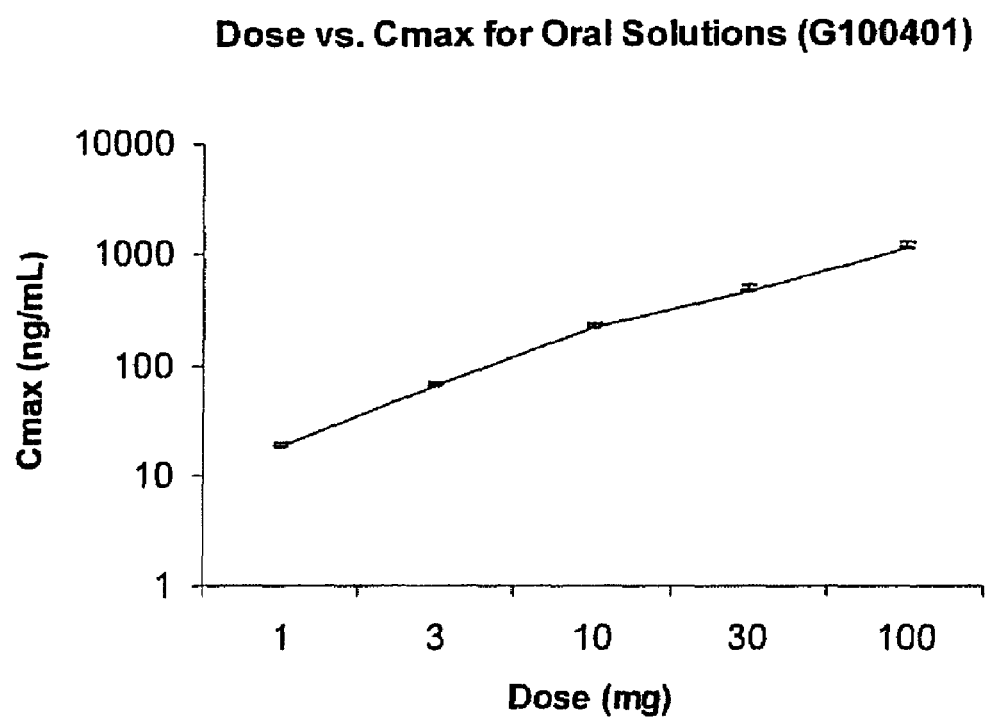
FIG. 14: Dose versus $C_{max}$ for oral solutions.

Doses of compound III in PEG300-based solutions at 1, 3, 10, 30 and 100 mg were rapidly absorbed from the gastrointestinal tract. All dose levels resulted in plasma compound III concentrations that were quantifiable through the last time point collected (72 hours) (FIG. 10-12). Exposure (Cmax and AUC) to compound III increased with increasing dose and was linear for solutions over the dose range 1 to 100 mg. $T_{max}$ was achieved between 0.8 and 2.3 hours (median value=1.0 hours) for compound III in solution, and between 3.2 and 3.9 hours following the solid oral formulations (FIGS. 13 & 14). The terminal elimination half-life ranged from 19 to 22 hours (median value=20 hours) for 1-100 mg solutions and the 3 mg capsule, and was increased with the 30 mg capsules to 27 and 31 hours for micronized and non-micronized, although not significantly (p>0.1). Oral clearance was inversely associated with half-life, with the 30 mg non-micronized capsule exhibiting the longest half-life and the lowest clearance compared to the other dosage forms and amounts. The 3 mg non-micronized capsule and solution were equally bioavailable, but at the higher dose (30 mg) micronization improved oral bioavailability (p<0.05) (FIG. 12). As suggested by a consistent second peak over the elimination phase of the drug, it is possible that enterohepatic recirculation through the hepatobiliary system plays a role in redistribution of parent drug.

Example 5

Anabolic and Androgenic Activity Of SARMs

Materials.

The SARMs are synthesized essentially in accordance with methods as described in U.S. Patent Application Publication No. 2004/0014975 A1 Alzet osmotic pumps (model 2002) are purchased from Alza Corp. (Palo Alto, Calif.).

The SARMs tested will comprise the following:

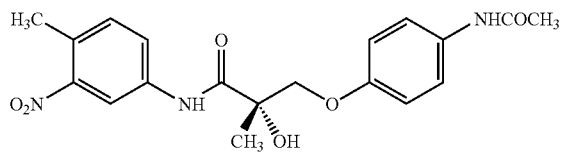

And

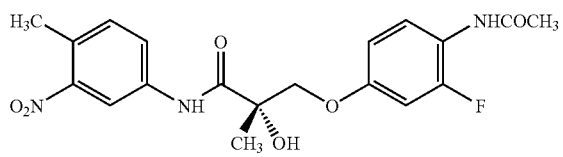

And their activity will be compared to that of:

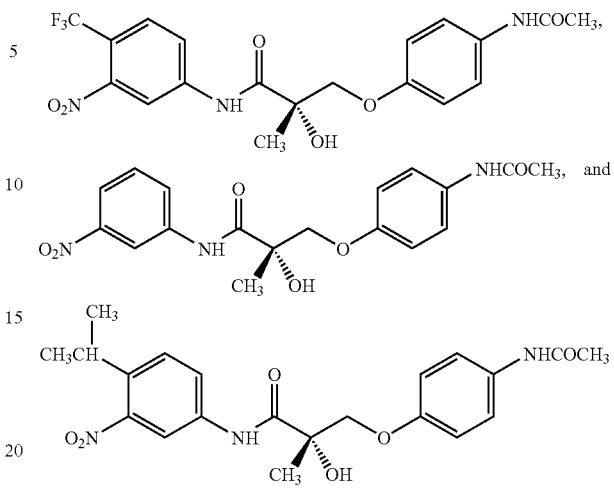

Study Design. Immature male Sprague-Dawley rats, weighing 90 to 100 g, are randomly distributed into groups, with at least 5 animals per group. One day prior to the start of drug treatment, animals are individually removed from the cage, weighed and anesthetized with an intraperitoneal dose of ketamine/xylazine (87/13 mg/kg; approximately 1 mL per kg). When appropriately anesthetized (i.e., no response to toe pinch), the animals' ears are marked for identification purposes. Animals are then placed on a sterile pad and their abdomen and scrotum washed with betadine and 70% alcohol. The testes ale removed via a midline scrotal incision, with sterile suture being used to ligate supra-testicular tissue prior to surgical removal of each testis. The surgical wound site is closed with sterile stainless steel wound clips, and the site cleaned with betadine. The animals are allowed to recover on a sterile pad (until able to stand) and then returned to their cage.

Twenty-four hours later, animals are re-anesthetized with ketamine/xylazine, and an Alzet osmotic pump(s) (model 2002) containing the SARM compound is placed subcutaneouly in the scapular region. Osmotic pumps contain the appropriate treatment (as described in Example 3) dissolved in polyethylene glycol 300 (PEG300). Osmotic pumps are filled with the appropriate solution one day prior to implantation. Animals are monitored daily for signs of acute toxicity to drug treatment (erg., lethargy, rough coat).

After 14 days of drug treatment, rats are anesthetized with ketamine/xylazine. Animals are sacrificed by exsanguination under anesthesia. A blood sample is collected by venipuncture of the abdominal aorta, and submitted for complete blood cell analysis. A portion of the blood is placed in a separate tube, centrifuged at 12,000 g for 1 minute, and the plasma layer removed and frozen at −20° C. The ventral prostates, seminal vesicles, levator ani muscle, liver, kidneys, spleen, lungs, and heart are removed, cleared of extraneous tissue, weighed, and placed in vials containing 10% neutral buffered formalin. Preserved tissues are subjected to histopathological analysis.

For data analysis, the weights of all organs are normalized to body weight, and analyzed for any statistical significant difference by single-factor ANOVA. The weights of prostate and seminal vesicle are used as indexes for evaluation of androgenic activity, and the levator ani muscle weight is used to evaluate the anabolic activity, Testosterone propionate (TP), at increasing doses, is used as the positive control of anabolic and androgenic effects. Effects of particular compounds may thus be compared to that of TP.

The weights of prostate, seminal vesicle, and levator ani muscle in castrated, vehicle-treated rats are expected to decrease significantly, due to the ablation of endogenous androgen production. Exogenous administration of testosterone propionate, an androgenic and anabolic steroid, are expected to increase the weights of prostate, seminal vesicle, and levator ani muscle in castrated rats in a dose-dependent manner. The SARMs will be comparatively evaluated for their effect on the weights of prostate, seminal vesicle, and levator ani muscle in castrated animals. Compounds which show lower potency and intrinsic activity in increasing the weights of prostate and seminal vesicle, but a greater potency and intrinsic activity in increasing the weight of levator ani muscle, will be considered to be poorly androgenic yet anabolic, and represent compounds which would be useful in therapy of, for example, prostate cancer, or for treating side effects associated with current therapies for prostate cancer, such as, for example, androgen deprivation therapy.

Example 6

SARM Reduction of Cholesterol Levels

Materials and Methods

One hundred Sprague Dawley rats (50 male and 50 female) were divided into five groups (n=10 per gender per group), representing vehicle only (PEG300:40% Cavasol® [75/25 (v/v)]), and four dose groups of Compound III. Animals were administered Compound III once daily by oral gavage according to their most recent body weight with doses of either 0, 3, 10, 30 or 100 mg/kg. During the study period, rats had access to water and a standard laboratory diet of Harlan Taklad Rodent Chow ad libitum. After 28 consecutive days of dosing, animals were fasted overnight, blood samples were collected and processed to yield serum. Serum levels of total cholesterol were determined using an automated laboratory assay method.

Results

Figure 15:
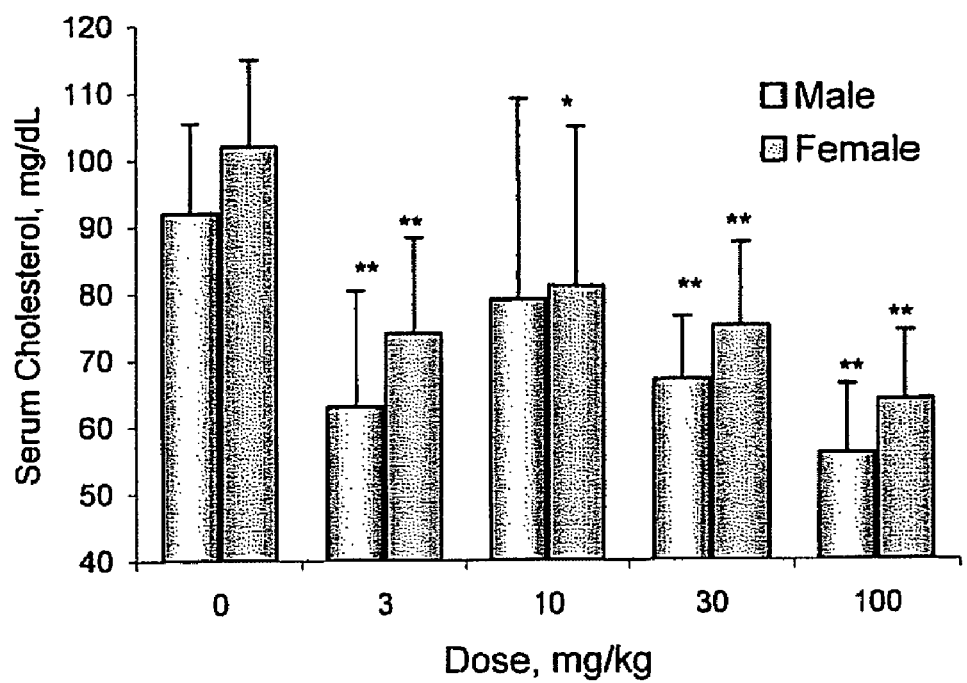
FIG. 15: Cholesterol reduction by compound III in rats.

The male and female rats in the vehicle only group (0 mg/kg) had serum total cholesterol values of 92±13.5 and 102±13 mg/dL respectively. These values are considered within the normal historical range for the testing laboratory. Daily oral doses of Compound III at or above 3 mg/kg caused a significant reduction in total cholesterol levels in both male and female rats. At 3 mg/kg, compared to vehicle control animals, al approximate 30% reduction in total cholesterol was noted where males and females had 63±17.4 and 74±14.2 mg/dL respectively. Although a slightly greater effect was noted at the highest dose group (100 mg/kg per day), in general, a dose-response relationship was not observed in the reduction of total cholesterol levels in the Sprague Dawley rat. Results are presented graphically in FIG. 15.

The effect of SARMs in causing acute toxicity, as gauged by diagnostic hematology tests and visual examination of animals receiving treatments will be assessed, as will suppression of luteinizing hormone (LH) or follicle stimulating hormone (FSH), as described in Example 4 hereinabove.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

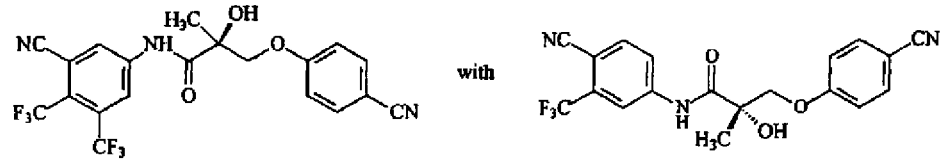

What is claimed is:

1. A method of treating a subject having a bone-related disorder, comprising the step of administering to said subject a SARM compound represented by a structure of formula (I), its pharmaceutically acceptable salt, or a combination thereof, or a composition comprising the same:

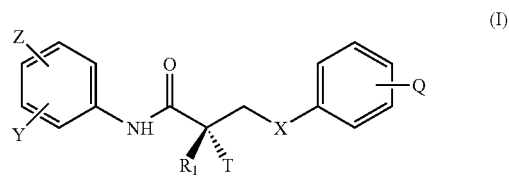

(I)

wherein
  X is O;
  Z is $NO_2$, CN, COR, or CONHR;
  Y is I, $CF_3$, Br, Cl, F or $Sn(R)_3$;
  Q is CN;
  T is OH, OR, —$NHCOCH_3$, NHCOR or OC(O)R;
  R is alkyl, haloalkyl, dihaloalkyl, trihaloalkyl, $CH_2F$, $CHF_2$, $CF_3$, $CF_2CF_3$, aryl, phenyl, halogen, alkenyl or OH; and
  $R_1$ is $CH_3$, $CH_2F$, $CHF_2$, $CH2CH_3$, or $CF_2CF_3$.

2. The method of claim 1, wherein said SARM compound is represented by a structure of formula (III), or its pharmaceutically acceptable salt, or any combination thereof, or a composition comprising the same,

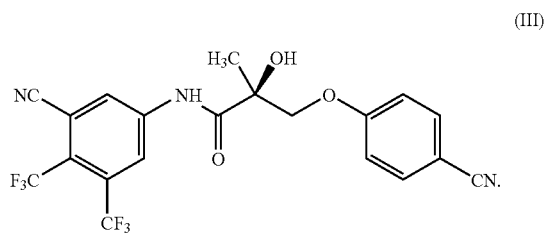

(III)

3. The method of claim 1, wherein said composition further comprises alendronate.

4. A method of increasing the strength of, or mass of a bone of a subject, or in promoting bone formation in a subject, comprising the step of administering to said subject a SARM compound represented by a structure of formula (I), its pharmaceutically acceptable salt, or any combination thereof, or a composition comprising the same:

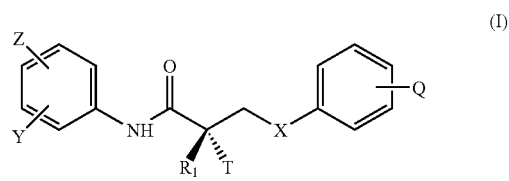

(I)

wherein
  X is O;
  Z is $NO_2$, CN, COR, or CONHR;
  Y is I, $CF_3$, Br, Cl, F or $Sn(R)_3$;

Q is CN;

T is OH, OR, —NHCOCH$_3$, NHCOR or OC(O)R;

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and R$_1$ is CH$_3$, CH$_2$F, CHF$_2$, CH$_2$CH$_3$, or CF2CF$_3$.

5. The method of claim 4, wherein said SARM compound is represented by a structure of formula (III), or its pharmaceutically acceptable salt, or any combination thereof, or a composition comprising the same

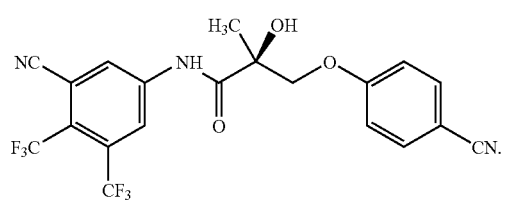

(III)

6. The method of claim 4, wherein said composition further comprises alendronate.

7. The method of claim 4, wherein said subject has sarcopenia or cachexia.

8. The method of claim 4, wherein said subject has osteoporosis.

9. The method of claim 4, wherein said osteoporosis is hormonally induced.

10. A method in the intervention of osteoperosois or osteopenia, comprising the step of administering to said subject a SARM compound represented by a structure of formula (I), its pharmaceutically acceptable salt, or any combination thereof, or a composition comprising the same:

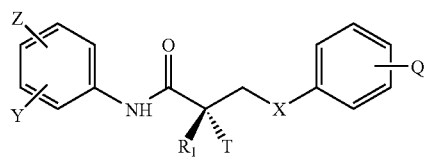

(I)

wherein

X is O;

Z is NO$_2$, CN, COR, or CONHR;

Y is I, CF$_3$, Br, Cl, F or Sn(R)$_3$;

Q is CN;

T is OH, OR, —NHCOCH$_3$, NHCOR or OC(O)R;

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and R$_1$ is CH$_3$, CH$_2$F, CHF$_2$, CH$_2$CH$_3$, or CF$_2$CF$_3$.

11. The method of claim 10, wherein said SARM compound is represented by a structure of formula (III), its pharmaceutically acceptable salt, or any combination thereof, or a composition comprising the same.

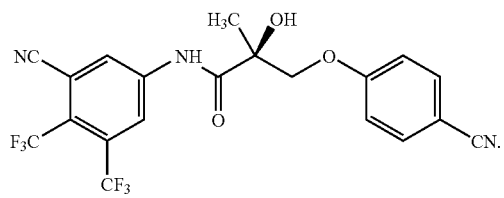

(III)

12. A method of treating, suppressing, inhibiting or reducing the incidence of a muscle wasting disorder in a subject comprising the step of administering to said subject a SARM compound represented by a structure of formula (I), its pharmaceutically acceptable salt, or any combination thereof, or a composition comprising the same:

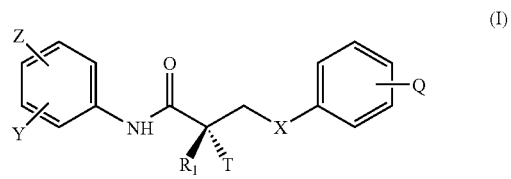

(I)

wherein

X is O;

Z is NO$_2$, CN, COR, or CONHR;

Y is I, CF$_3$, Br, Cl, F or Sn(R)$_3$;

Q is CN;

T is OH, OR, —NHCOCH$_3$, NHCOR or OC(O)R;

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and R$_1$ is CH$_3$, CH$_2$F, CHF$_2$, CH$_2$CH$_3$, or CF$_2$CF$_3$.

13. The method of claim 12, wherein said SARM compound is represented by a structure of formula (III), its pharmaceutically acceptable salt, or any combination thereof or a composition comprising the same,

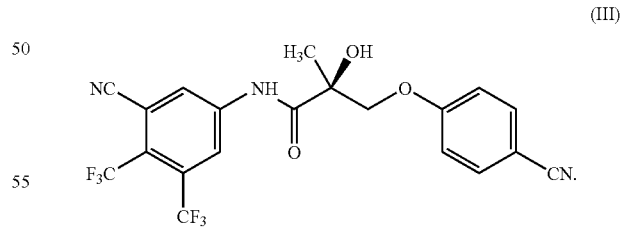

(III)

14. The method of claim 12, wherein said muscle wasting disorder is due to a pathology, illness, disease or condition.

15. A method in increasing muscle performance, muscle size, muscle strength, or any combination thereof in a subject comprising the step of administering to said subject a SARM compound represented by a structure of formula (I), its pharmaceutically acceptable salt, or any combination thereof, or a composition comprising the same:

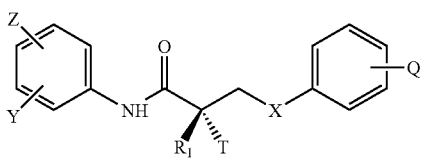

(I)

wherein
X is O;
Z is NO$_2$, CN, COR, or CONHR;
Y is I, CF$_3$, Br, Cl, F or Sn(R)$_3$;
Q is CN;
T is OH, OR, —NHCOCH$_3$, NHCOR or OC(O)R;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is CH$_3$, CH$_2$F, CHF$_2$, CH$_2$CH$_3$, or CF$_2$CF$_3$.

16. The method of claim 15, wherein said SARM compound is represented by a structure of formula (III), its pharmaceutically acceptable salt, or any combination thereof, or a composition comprising the same,

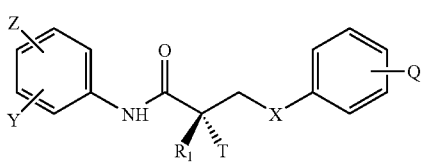

(III)

17. A method in treating obesity or diabetes associated with a metabolic syndrome in a subject comprising the step of administering to said subject a SARM compound represented by a structure of formula (I), its pharmaceutically acceptable salt, or any combination thereof, or a composition comprising the same:

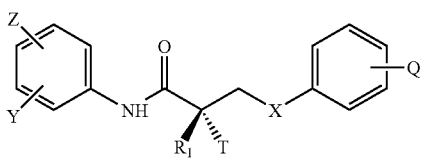

(I)

wherein
X is O;
Z is NO$_2$, CN, COR, or CONHR;
Y is I, CF$_3$, Br, Cl, F or Sn(R)$_3$;
Q is CN;
T is OH, OR, —NHCOCH$_3$, NHCOR or OC(O)R;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is CH$_3$, CH$_2$F, CHF$_2$, CH$_2$CH$_3$, or CF$_2$CF$_3$.

18. The method of claim 17, wherein said SARM compound is represented by a structure of formula (III), its pharmaceutically acceptable salt, or any combination thereof, or a composition comprising the same,

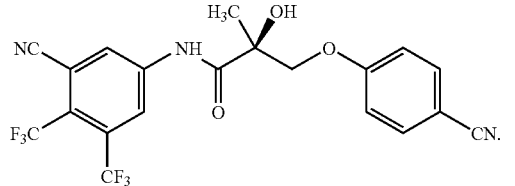

(III)

19. The method of claim 17, wherein said subject has a hormonal imbalance, disorder, or disease.

20. The method of claim 17, wherein said subject is in menopause.

21. The method of claim 17, wherein said SARM increases lean mass in the subject.

22. A method in promoting or speeding recovery following a surgical procedure, in a subject comprising the step of administering to said subject a SARM compound represented by a structure of formula (I), its pharmaceutically acceptable salt, or any combination thereof, or a composition comprising the same:

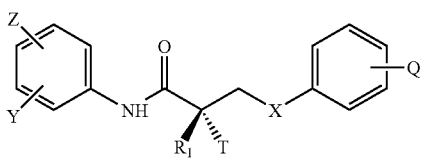

(I)

wherein
X is O;
Z is NO$_2$, CN, COR, or CONHR;
Y is I, CF$_3$, Br, Cl, F or Sn(R)$_3$;
Q is CN;
T is OH, OR, —NHCOCH$_3$, NHCOR or OC(O)R;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is CH$_3$, CH$_2$F, CHF$_2$, CH$_2$CH$_3$, or CF$_2$CF$_3$.

23. The method of claim 22, wherein said SARM compound is represented by a structure of formula (III), its pharmaceutically acceptable salt, or any combination thereof, or a composition comprising the same,

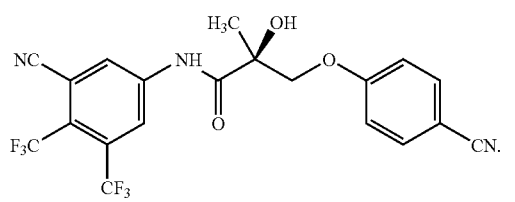

(III)

* * * * *

UNITED STATES PATENT AND TRADEMARK OFFICE
CERTIFICATE OF CORRECTION

PATENT NO. : 7,622,503 B2  
APPLICATION NO. : 11/146427  
DATED : November 24, 2009  
INVENTOR(S) : James T. Dalton et al.

It is certified that error appears in the above-identified patent and that said Letters Patent is hereby corrected as shown below:

Claim 1 (col. 36, line 29): "CH2CH₃" should be --CH₂CH₃--

Claim 2 (col. 36, lines 35-45): replace

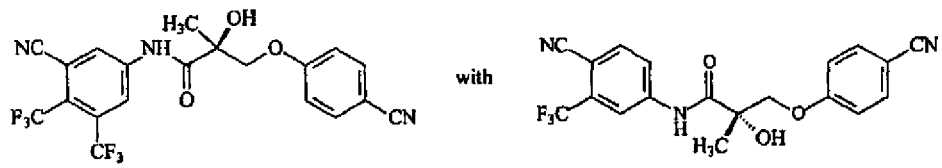

Claim 5 (col. 37, lines 13-24): replace

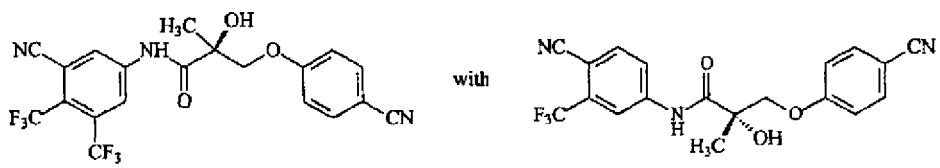

Claim 11 (col. 38, lines 1-10): replace

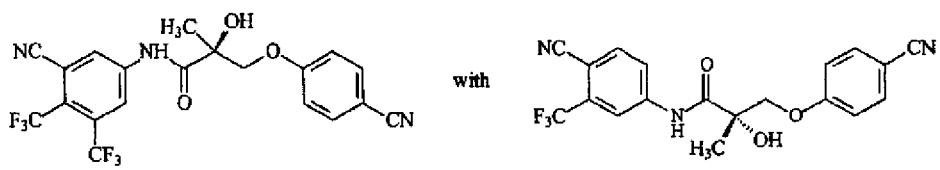

Claim 16 (col. 39, lines 25-35): replace

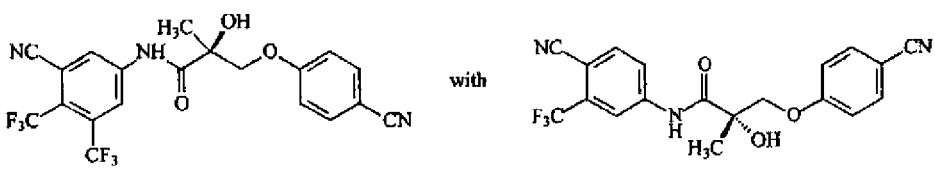

Claim 18 (col. 40, lines 3-14): replace

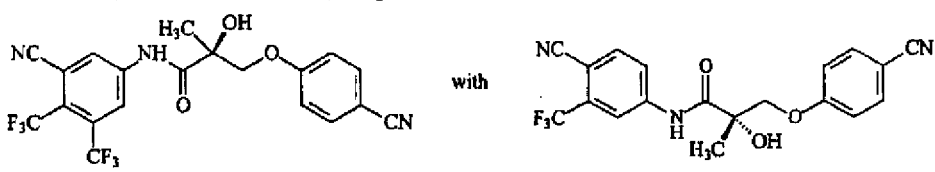

CERTIFICATE OF CORRECTION (continued)
U.S. Pat. No. 7,622,503 B2

Claim 23 (col. 40, lines 51-60): replace